US012668763B2

(12) United States Patent
Shimizu et al.

(10) Patent No.: US 12,668,763 B2
(45) Date of Patent: Jun. 30, 2026

(54) CO-CULTURING DEVICE, MOTOR NEURON CULTURING DEVICE, MULTI-WELL PLATE, FABRICATION METHOD OF IN VITRO EVALUATION MODEL OF NEUROMUSCULAR DISEASE, AND SCREENING METHOD OF THERAPEUTIC AGENT AGAINST NEUROMUSCULAR DISEASE

(71) Applicant: National University Corporation Tokai National Higher Education and Research System, Aichi (JP)

(72) Inventors: Kazunori Shimizu, Nagoya (JP); Hiroyuki Honda, Nagoya (JP); Nao Yamaoka, Nagoya (JP)

(73) Assignee: National University Corporation Tokai National Higher Education and Research System, Aichi (JP)

( * ) Notice: Subject to any disclaimer, the term of this patent is extended or adjusted under 35 U.S.C. 154(b) by 1323 days.

(21) Appl. No.: 17/431,992

(22) PCT Filed: Feb. 18, 2020

(86) PCT No.: PCT/JP2020/006221
§ 371 (c)(1),
(2) Date: Aug. 18, 2021

(87) PCT Pub. No.: WO2020/171052
PCT Pub. Date: Aug. 27, 2020

(65) Prior Publication Data
US 2021/0380913 A1      Dec. 9, 2021

(30) Foreign Application Priority Data
Feb. 20, 2019    (JP) ................................. 2019-028451

(51) Int. Cl.
*C12M 3/00*      (2006.01)
*C12M 1/00*      (2006.01)
(Continued)

(52) U.S. Cl.
CPC ............ *C12M 21/08* (2013.01); *C12M 23/12* (2013.01); *C12M 23/34* (2013.01); *C12M 25/14* (2013.01);
(Continued)

(58) Field of Classification Search
CPC ...... C12M 21/08; C12M 23/12; C12M 23/34; C12M 25/14; C12M 23/16; C12M 23/58;
(Continued)

(56) References Cited

U.S. PATENT DOCUMENTS

2017/0355945 A1    12/2017   Kamm et al.
2021/0380913 A1*   12/2021   Shimizu ............. G01N 33/5082

FOREIGN PATENT DOCUMENTS

JP        2019-000093 A      1/2019

OTHER PUBLICATIONS

Y. Morimoto et al., "Three-dimensional neuronemuscle constructs with neuromuscular junctions," Biomaterials 34, (2013); pp. 9413-9419.
(Continued)

*Primary Examiner* — Tracy Vivlemore
*Assistant Examiner* — Thomas R. Amick
(74) *Attorney, Agent, or Firm* — Rimon P.C.

(57)        ABSTRACT

A device includes a first unit for skeletal muscle tissue formation; a second unit for motor neuron culture; a third unit for causing the first and second units to communicate with each other; and a pillar serving as a scaffold for skeletal muscle tissue formation. The first unit includes a first base material and a first culture tank formed in the first base material. The second unit includes a second base material
(Continued)

and a second culture tank formed in the second base material. The third unit includes a third base material and an axon channel formed in the third base material, through which a bundle of axons passes. One end of the third unit is connectable to the second unit and cause the axon channel and the second culture tank to communicate with each other. A first opening part is formed to the other end of the third unit.

15 Claims, 13 Drawing Sheets

(51) Int. Cl.
    *C12M 1/12*          (2006.01)
    *C12M 1/32*          (2006.01)
    *G01N 33/50*        (2006.01)

(52) U.S. Cl.
    CPC ..... *G01N 33/5058* (2013.01); *G01N 33/5082* (2013.01)

(58) Field of Classification Search
    CPC ... C12M 25/00; C12M 35/08; G01N 33/5058; G01N 33/5082; G01N 33/15; G01N 37/00
    See application file for complete search history.

(56) References Cited

OTHER PUBLICATIONS

Osaki, T. et al., "Microphysiological 3D model of amyotrophic lateralsclerosis (ALS) from human iPS-derived muscle cells and optogenetic motor neurons," Science Advances, Oct. 10, 2018, pp. 1-15.

International Search Report and Written Opinion issued in International Patent Application No. PCT/JP2020/006221, dated May 26, 2020; with partial English translation.

Yamaoka, N. et al., "Open-Chamber Co-Culture Microdevices for Single-Cell Analys is of Skeletal Muscle Myotubes an d Motor Neurons with Neuromuscular Junctions.", BioChip Journal, Apr. 1, 2019, vol. 13, No. 2, pp. 127-132.

English translation of International Preliminary Report on Patentability, issued in International Patent Application No. PCT/JP2020/006221, issued on Aug. 3, 2021.

* cited by examiner

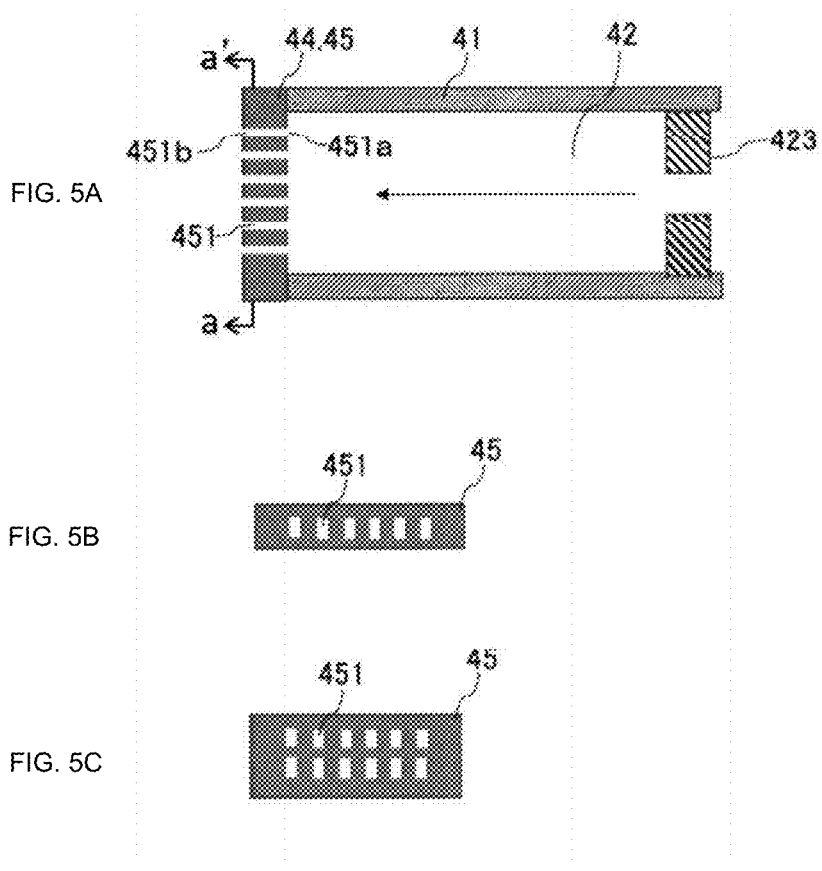
FIG. 5A
FIG. 5B
FIG. 5C
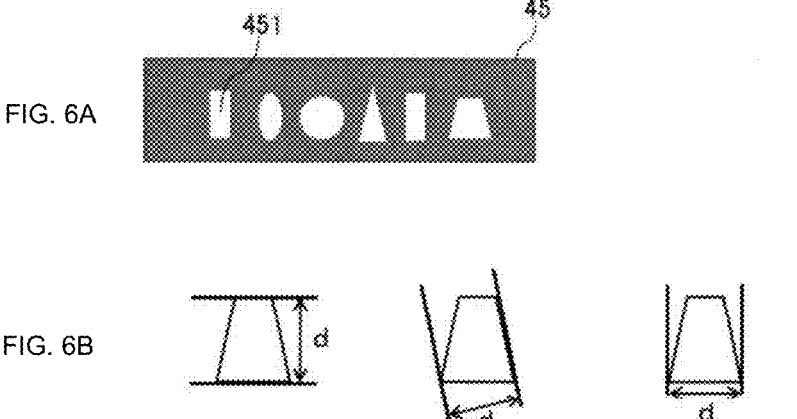
FIG. 6A
FIG. 6B 1.1c 1.1d

FIG. 15A
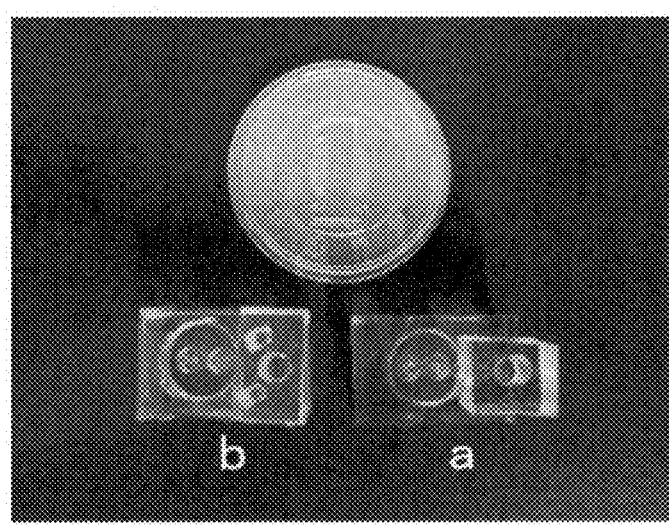
FIG. 15B
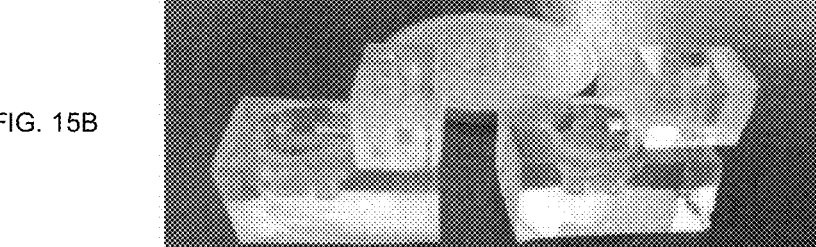
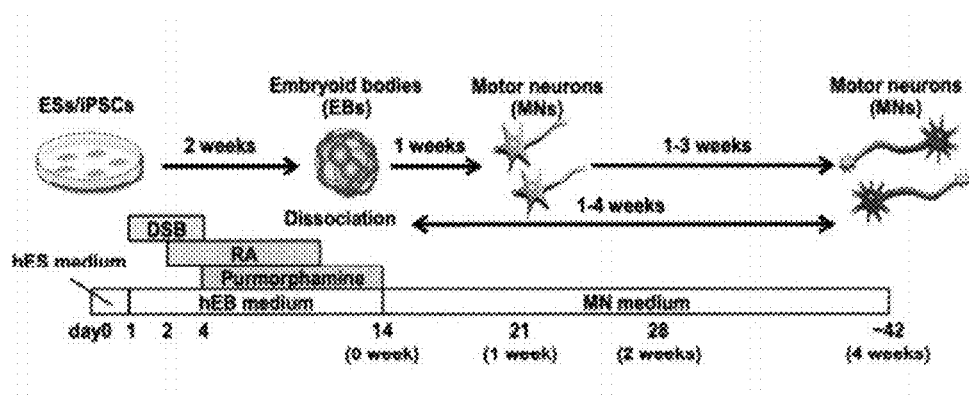
FIG. 16

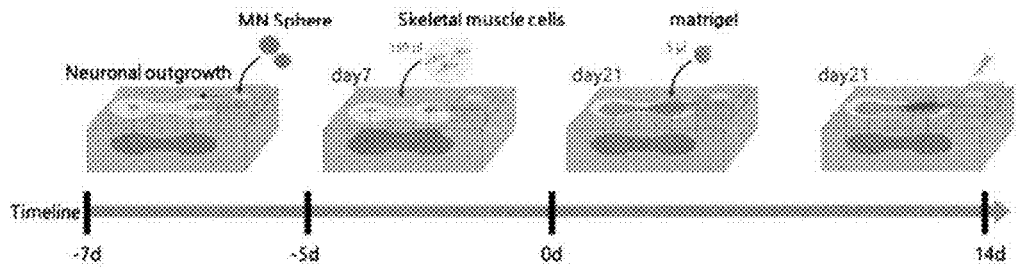
FIG. 17
FIG. 18A
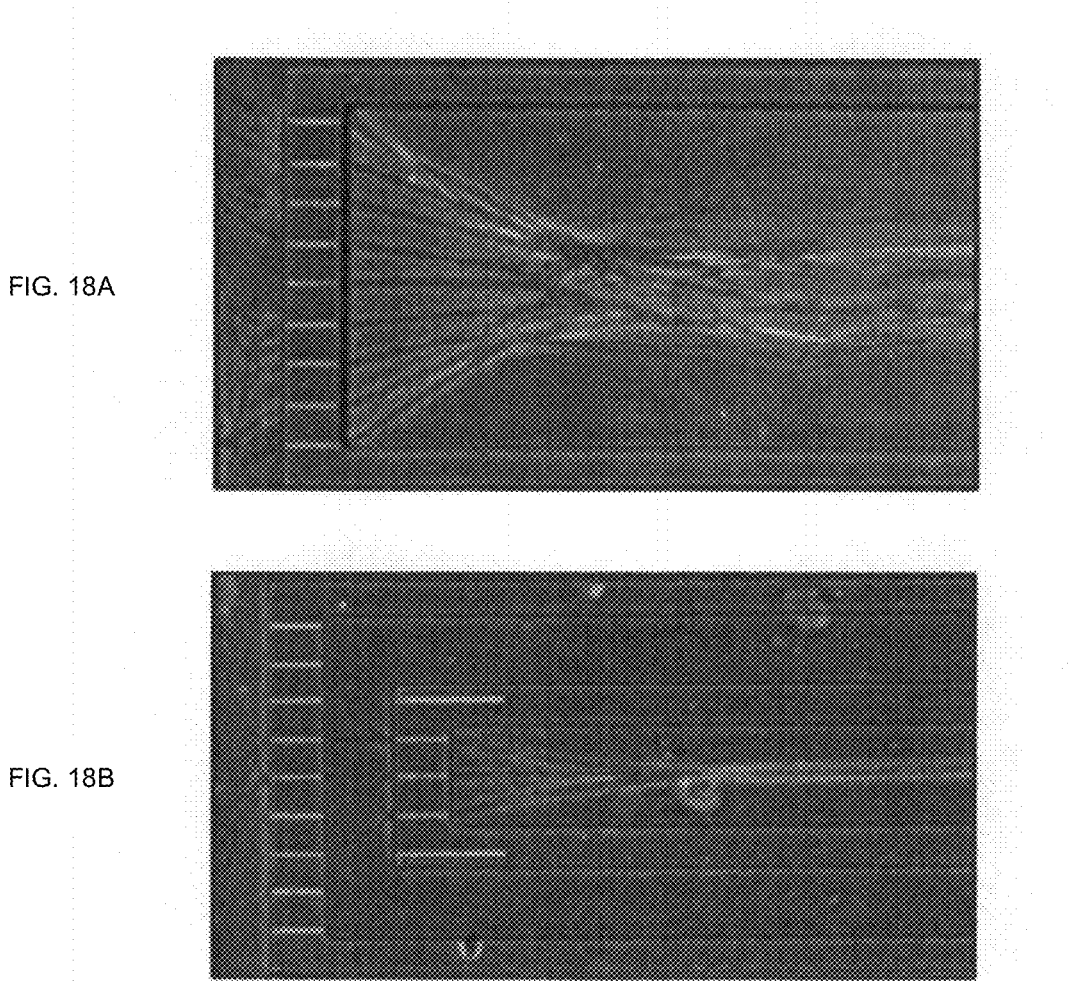
FIG. 18B

FIG. 21A
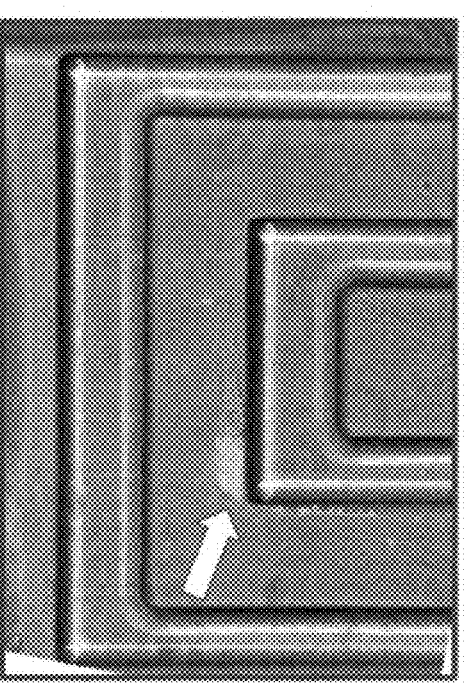
FIG. 21B
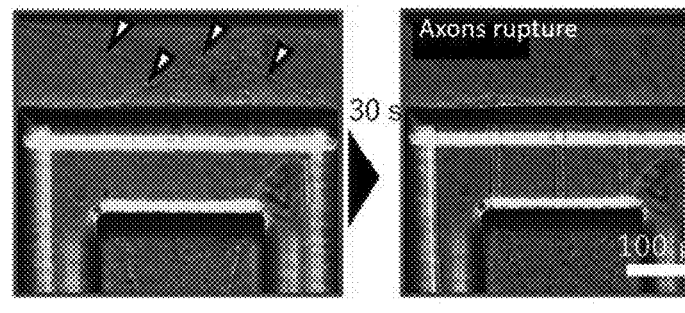
FIG. 22A
FIG. 22B
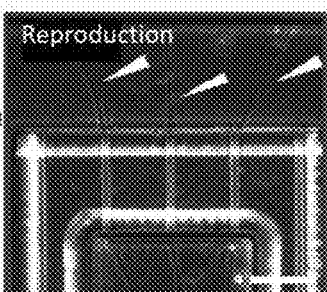
FIG. 22C

CO-CULTURING DEVICE, MOTOR NEURON CULTURING DEVICE, MULTI-WELL PLATE, FABRICATION METHOD OF IN VITRO EVALUATION MODEL OF NEUROMUSCULAR DISEASE, AND SCREENING METHOD OF THERAPEUTIC AGENT AGAINST NEUROMUSCULAR DISEASE

CROSS-REFERENCE OF RELATED APPLICATIONS

This application is the U.S. National Phase under 35 U.S.C. § 371 of International Patent Application No. PCT/JP2020/006221, filed on Feb. 18, 2020, which in turn claims the benefit of Japanese Application No. 2019-028451, filed on Feb. 20, 2019, the entire disclosures of which Applications are incorporated by reference herein.

TECHNICAL FIELD

The disclosure of the present application relates to a co-culturing device, a motor neuron culturing device, a multi-well plate, a fabrication method of an in vitro evaluation model of a neuromuscular disease, and a screening method of a therapeutic agent against a neuromuscular disease. More specifically, the disclosure relates to a co-culturing device and a motor neuron culturing device used for fabricating an in vitro evaluation model of a neuromuscular disease closer to the human body structure, a multi-well plate in which a device is arranged in each well, and a screening method of a therapeutic agent against a neuromuscular disease using the in vitro evaluation model of the neuromuscular disease.

BACKGROUND ART

In various neuromuscular diseases, degeneration of motor neurons and skeletal muscle cells or an anomaly of a neuromuscular junction (NMJ) that is a junction between a motor neuron and a skeletal muscle tissue causes a progressive life-threatening motor dysfunction. As an example of neuromuscular diseases, Amyotrophic Lateral Sclerosis (ALS), Spinal and Bulbar Muscular Atrophy (SBMA), and the like are known.

Devices (evaluation models) for performing in vitro study of a disease developing mechanism or screening of a therapeutic agent for neuromuscular diseases are known. For example, a technology to, first, culture skeletal muscle cells to fabricate a skeletal muscle tissue and then culture motor neurons thereon is known (see Non-Patent Literature 1). In the method disclosed in Non-Patent Literature 1, however, there is a problem of a difference from the actual structure in a human body because of a mixed state of the skeletal muscle tissue and the motor neurons.

FIG. 1 is a diagram illustrating another example of a conventional art of a device (evaluation model) (see Non-Patent Literature 2). In the example of the device illustrated in FIG. 1, a skeletal muscle tissue forming section and a motor neuron section are divided by using PDMS. In the example illustrated in FIG. 1, first, skeletal muscle cells are cultured in the skeletal muscle tissue forming section to fabricate a skeletal muscle tissue (reference A). Next, a motor neuron spheroid containing collagen gel is supplied to the motor neuron section (reference B). Note that a plurality of pillars (reference P) used for arranging the motor neuron spheroid at a predetermined position are provided in the motor neuron section. Further, by continuing the culture, an axon (reference C) extending from the motor neuron is coupled to the skeletal muscle tissue, and thereby a neuromuscular junction can be formed.

CITATION LIST

Non-Patent Literature

[Non-Patent Literature 1] Y. Morimoto et al., "Three-dimensional neuronemuscle constructs with neuromuscular junctions", Biomaterials 34 (2013) 9413-9419
[Non-Patent Literature 2] T. Osaki et al., "Microphysiological 3D model of amyotrophic lateralsclerosis (ALS) from human iPS-derived muscle cells and optogenetic motor neurons", Sci. Adv. 2018; 4:eaat5847

SUMMARY OF INVENTION

Technical Problem

In a device (evaluation model) disclosed in Non-Patent Literature 2, motor neurons and a skeletal muscle tissue are three-dimensionally arranged, and furthermore, collagen gel is used as a scaffold for extension of an axon. Thus, the collagen gel is required to be added to a skeletal muscle tissue forming section, a motor neuron section, and a channel that connects the skeletal muscle tissue forming section and the motor neuron section to each other.

As described above, however, the device (evaluation model) disclosed in Non-Patent Literature 2 requires the periphery of the motor neuron and the skeletal muscle tissue to be covered with the collagen gel serving as a scaffold. Thus, even with fabrication of an evaluation model in which a neuromuscular junction is formed by using the device disclosed in Non-Patent Literature 2, there is a problem of fusion of the motor neurons and the skeletal muscle tissue because a motor neuron spheroid grows so as to climb over the pillars and the skeletal muscle tissue also grows and expands as illustrated in FIG. 2 as time elapses. Further, in the evaluation model disclosed in Non-Patent Literature 2, the skeletal muscle tissues and the like are formed in the collagen gel. Thus, there is a problem of the movement of the skeletal muscle tissue being suppressed by the collagen gel. Furthermore, since it is necessary to observe the movement of a skeletal muscle tissue via the collagen gel when observing movement of the skeletal muscle tissue, there is a problem of difficulty in observing the movement of the skeletal muscle tissue.

The disclosure in the present application has been made to solve the problems described above, and intensive studies of devices (evaluation models) using no collagen gel as a scaffold have newly found that (1) a first unit for skeletal muscle tissue formation having a first culture tank to which a culture medium can be added, (2) a second unit for motor neuron culture having a second culture tank to which a culture medium can be added, and (3) a third unit that causes the first unit to communicate with the second unit are included, and (4) an opening part in which an axon passage hole through which an axon can pass but neither a motor neuron nor a skeletal muscle cell can pass is formed is provided in the third unit, and thereby, an in vitro evaluation model of a neuromuscular disease using the third unit as a scaffold through which the axon can pass can be fabricated.

That is, the object of the disclosure in the present application is to provide a co-culturing device, a motor neuron culturing device, a multi-well plate, a fabrication method of an in vitro evaluation model of a neuromuscular disease, and a screening method of a therapeutic agent against a neuromuscular disease.

Solution to Problem

The disclosure in the present application relates to a co-culturing device, a motor neuron culturing device, a multi-well plate, a fabrication method of an in vitro evaluation model of a neuromuscular disease, and a screening method of a therapeutic agent against a neuromuscular disease illustrated below.

(1) A co-culturing device for a motor neuron and a skeletal muscle cell, the device comprising:
a first unit for skeletal muscle tissue formation;
a second unit for motor neuron culture;
at least one third unit for causing the first unit and the second unit to communicate with each other; and
at least one pillar serving as a scaffold for the skeletal muscle tissue formation,
wherein the first unit includes
a first base material, and
a first culture tank formed in the first base material,
wherein the second unit includes
a second base material, and
a second culture tank formed in the second base material,
wherein the third unit includes
a third base material, and
an axon channel which is formed in the third base material and through which a bundle of axons passes,
wherein one end part of the third unit is configured to be connected to the second unit and configured to cause the axon channel and the second culture tank to communicate with each other when the one end part of the third unit is connected to the second unit,
wherein a first opening part is formed to the other end part of the third unit so as to be in contact with the axon channel, and one or more first axon passage holes are formed in the first opening part,
wherein the first axon passage hole has a size through which an axon passes while neither a motor neuron nor a skeletal muscle cell passes, and
wherein at least a part of the pillar is arranged in the first culture tank.

(2) The device according to (1) above,
wherein the axon channel includes
a first channel, and
a second channel formed inside the first channel,
wherein the first opening part is formed so as to be in contact with the first channel,
wherein one end of the second channel is configured to communicate with the second culture tank, and a second opening part is formed to and in contact with the other end of the second channel,
wherein one or more second axon passage holes are formed in the second opening part, and each of the second axon passage holes has a size through which an axon passes while neither a motor neuron nor a skeletal muscle cell passes, and
wherein the first opening part and the second opening part are arranged spaced apart from each other.

(3) The device according to (1) or (2) above, wherein two or more third units are stacked.

4

(4) The device according to any one of (1) to (3) above,
wherein a positional relationship of the first unit, the second unit, the one or more third units, and the pillar is arranged such that
when two or more pillars are included, any of virtual planes connecting the two or more pillars intersects a virtual axon channel of the axon channel virtually extending to the first culture tank, or
when only one pillar is provided, a virtual plane formed by the one pillar or a virtual plane formed by the pillar and the other end part of the third unit intersects a virtual axon channel of the axon channel virtually extending to the first culture tank.

(5) The device according to (4) above, wherein two pillars are included, one end of each of the pillars is connected to the first base material, and the other end is arranged in the first culture tank in a cantilevered manner.

(6) The device according to any one of (1) to (5) above, wherein the size of the first axon passage hole is formed such that
the minimum distance is greater than or equal to 0.5 $\mu m$ and less than or equal to 2.5 $\mu m$, or
the minimum distance is greater than or equal to 0.5 $\mu m$, and the sectional area is less than or equal to 60 $\mu m^2$.

(7) The device according to any one of (1) to (6) above,
wherein motor neuron culturing devices are each fabricated by the second unit and the third unit being connected to each other, and
wherein two or more of the motor neuron culturing devices are arranged to the first unit.

(8) The device according to any one of (1) to (6) above,
wherein a motor neuron culturing device is fabricated by connecting two or more third units to the second unit, and
wherein the first unit is arranged to the other end of any of the third units.

(9) A motor neuron culturing device used in a co-culturing device for a motor neuron and a skeletal muscle cell, the motor neuron culturing device comprising:
a second unit for motor neuron culture; and
a third unit connected to the second unit,
wherein the second unit includes
a second base material, and
a second culture tank formed in the second base material,
wherein the third unit includes
a third base material, and
an axon channel which is formed in the third base material and through which a bundle of axons passes,
wherein one end of the third unit and the second unit are connected to each other, and one end of the axon channel communicates with the second culture tank,
wherein a first opening part is formed to the other end part of the third unit so as to be in contact with the axon channel, and one or more first axon passage holes are formed in the first opening part, and
wherein the first axon passage hole has a size through which an axon passes while neither a motor neuron nor a skeletal muscle cell passes.

(10) A multi-well plate comprising at least two or more wells, wherein the device according to any one of (1) to (9) above is arranged in at least one of the wells.

(11) A fabrication method of an in vitro evaluation model for a neuromuscular disease using the device according to any one of (1) to (8) above, the fabrication method comprising:

a motor neuron culture step of culturing a motor neuron in a second unit;

a skeletal muscle tissue fabrication step of culturing a skeletal muscle cell in a first unit and fabricating a skeletal muscle tissue; and a neuromuscular junction fabrication step of fabricating a neuromuscular junction by causing an axon extending from a cell body of the cultured motor neuron to pass through an axon channel of a third unit and join to the fabricated skeletal muscle tissue.

(12) A screening method of a therapeutic agent against a neuromuscular disease using an in vitro evaluation model for a neuromuscular disease fabricated by the fabrication method according to (11) above, the screening method comprising:

a test substance administration step of administering a test substance to any one of a motor neuron, an axon extending from a cell body of the motor neuron, and a skeletal muscle tissue of the fabricated evaluation model;

a measurement step of measuring a state of at least one of the motor neuron, the axon extending from the cell body of the motor neuron, and the skeletal muscle tissue; and a test substance evaluation step of evaluating from a result of the measurement step whether or not the test substance works as a therapeutic agent against the neuromuscular disease.

Advantageous Effect

The evaluation model fabricated by using the co-culturing device disclosed in the present application does not use collagen as a scaffold. This therefore facilitates observation of movement of a skeletal muscle tissue or the like.

BRIEF DESCRIPTION OF DRAWINGS

FIG. 3A, FIG. 3B, FIG. 3C, FIG. 3D, FIG. 3E, FIG. 3F, FIG. 3G, and FIG. 3H are diagrams illustrating an overview of a device 1a.

FIG. 4A, FIG. 4B and FIG. 4C are diagrams illustrating an example of other embodiments of connection between a second unit and one end part of a third unit of the device 1a.

FIG. 5A, FIG. 5B and FIG. 5C are diagrams illustrating the third unit in more detail.

FIG. 6A and FIG. 6B are diagrams illustrating a first opening face and a second opening face of the device 1a in more detail.

FIG. 15A and FIG. 15B are photograph substitutes for drawings, which represent photographs of a device fabricated in Example 1.

FIG. 16 is a diagram illustrating an overview of differentiation induction in fabrication of an evaluation model in Example 2.

FIG. 17 is a diagram illustrating a procedure of co-culture in the fabrication of the evaluation model of Example 2.

FIG. 18A and FIG. 18B are photograph substitutes for drawings, which represent enlarged photographs near a first opening part of a third unit of an evaluation model fabricated in Example 2.

FIG. 21A and FIG. 21B are photograph substitutes for drawings, which represent photomicrographs after an axon of the evaluation model fabricated in Example 2 is stained.

FIG. 22A, FIG. 22B and FIG. 22C are photograph substitutes for drawings, which represent photomicrographs used for confirming rupture and reproduction of axons of Example 3.

DESCRIPTION OF EMBODIMENTS

Each embodiment of a co-culturing device (hereafter, which may be simply referred to as a "device"), a motor neuron culturing device, a multi-well plate, a fabrication method of an in vitro evaluation model of a neuromuscular disease (hereafter, which may be simply referred to as a "fabrication method of an evaluation model"), and a screening method of a therapeutic agent against a neuromuscular disease (hereafter, which may be simply referred to as a "screening method") will be described below in detail with reference to the drawings. Note that, in the present specification, members having the same type of function are labeled with the same or similar references. Further, duplicated description of members labeled with the same or similar references may be omitted.

[First Embodiment of Device]

Figures 3A, 3B, 3C, 3D, 3E, 3F, 3G, 3H:
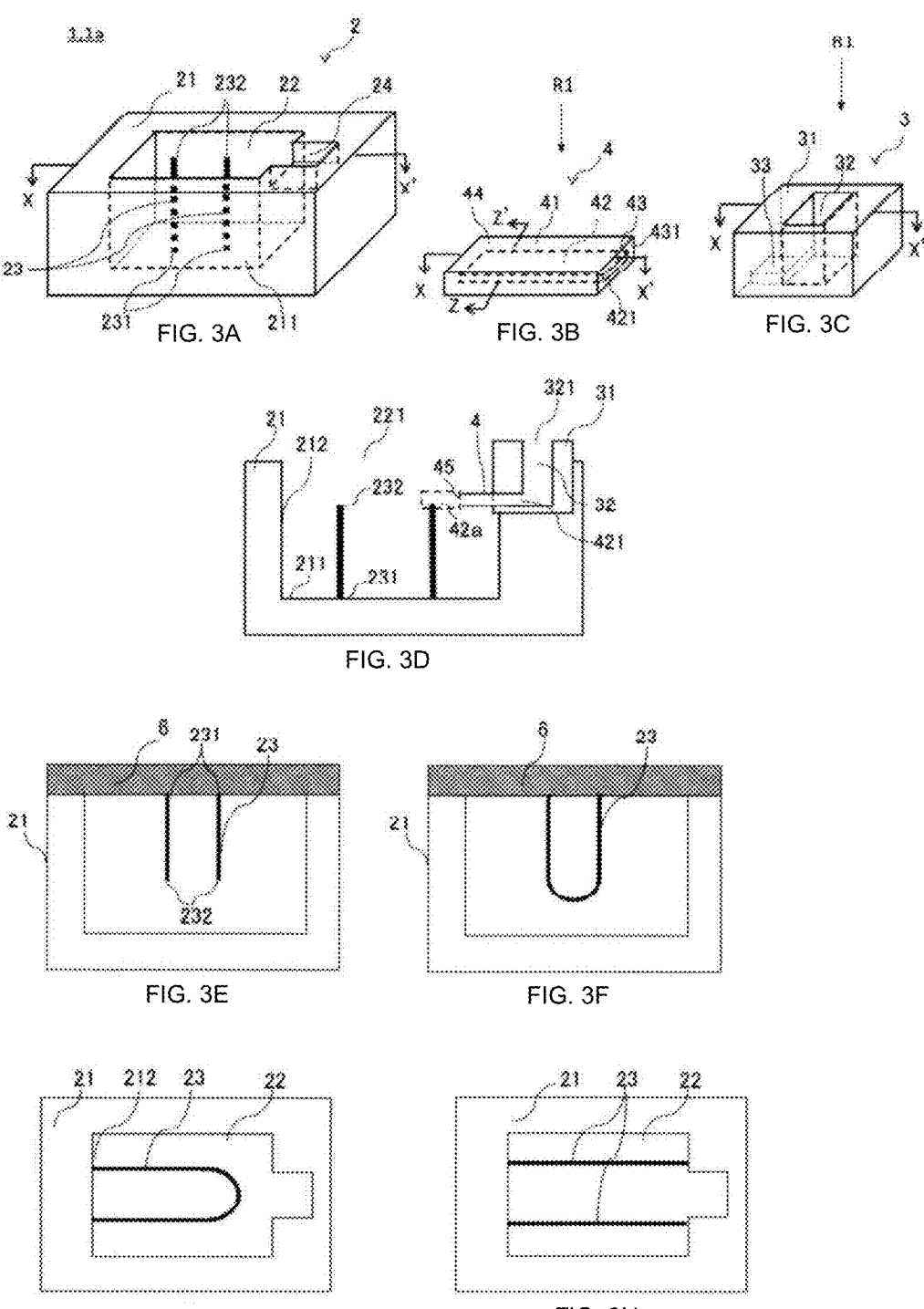

A device 1a according to a first embodiment will be described with reference to FIG. 3. FIG. 3 includes diagrams illustrating an overview of the device 1a. The device 1a according to the first embodiment includes a first unit 2 for skeletal muscle tissue formation, a second unit 3 for motor neuron culture, a third unit 4 for causing the first unit 2 communicates with the second unit, and pillars 23. FIG. 3A is a diagram illustrating the overview of the first unit 2, FIG. 3B is a diagram illustrating the overview of the third unit 4, and FIG. 3C is a diagram illustrating the overview of the second unit 3. Further, FIG. 3D is a schematic sectional view taken along the direction X-X' when the first unit 2, the second unit 3, and the third unit 4 are combined to fabricate the device 1a. FIG. 3E and FIG. 3F are schematic sectional views illustrating other embodiments of the pillar 23, which are sectional views taken along the direction orthogonal to the direction X-X' of FIG. 3A. FIG. 3G and FIG. 3H are schematic diagrams illustrating other embodiments of the pillar 23, which are top views (diagrams in the R1 direction in FIG. 3A) of the first unit 2.

The first unit 2 will be described in more detail with reference to FIG. 3A and FIG. 3D. The first unit 2 includes a first base material 21 and a first culture tank 22. Further, FIG. 3A and FIG. 3D illustrate an example in which the pillars 23 are attached to the first unit 2. The first culture tank 22 is used for culturing skeletal muscle cells and forming a skeletal muscle tissue from the cultured skeletal muscle cells. The first culture tank 22 is formed in the first base material 21 and, in the example illustrated in FIG. 3A and FIG. 3D, formed in substantially a recess shape having a first culture medium supply hole 221 in the upper face of substantially a rectangular parallelepiped first base material 21.

In the example illustrated in FIG. 3A and FIG. 3D, the pillars 23 are used for forming a skeletal muscle tissue from skeletal muscle cells cultured in the first culture tank 22. Each pillar 23 has one end 231 connected to a wall surface forming the first culture tank 22 of the first base material 21 and the other end 232 arranged in the first culture tank 22. In other words, the pillar 23 is arranged in a cantilevered state. Thus, skeletal muscle cells are cultured in the first culture tank 22, a skeletal muscle tissue formed at the other end 232 of the pillar 23 is formed three-dimensionally in the first culture tank 22, in other words, formed in a floating state in the first culture tank 22. That is, this is different from a case where a skeletal muscle tissue is formed on a plane, in other words, a skeletal muscle tissue is formed two-dimensionally. Therefore, FIG. 3A and FIG. 3D illustrate an example in which two pillars 23 are provided. With the two pillars 23 being provided, the formed skeletal muscle tissue can be oriented in a direction connecting the pillars 23, and a tissue closer to a skeletal muscle tissue of a human body can be formed. Note that three or more pillars 23 may be provided. In such a case, when fabricated skeletal muscle tissues are intended to be oriented in the same direction, the three or more pillars 23 can be arranged linearly. Further, the interval of the pillars 23 is not particularly limited as long as the skeletal muscle tissue can be formed between the pillars 23 and may be, for example, 0.5 mm to 5 mm, 1 mm to 3.5 mm, or 1.5 mm to 2.6 mm. Note that, in the present specification, an expression of XX μm to YY μm means "greater than or equal to XX μm and less than or equal to YY μm".

In the example illustrated in FIG. 3A and FIG. 3D, the one end 231 of each pillar 23 is formed on the bottom 211 of the first base material 21 (a wall surface of the first base material 21 on the opposite side from the first culture medium supply hole 221 of the first culture tank 22). Alternatively, the one end 231 may be formed to a part other than the bottom 211, for example, a side wall surface 212 of the first base material 21 as long as the pillar 23 is formed in a cantilevered manner such that the other end 232 is arranged in the first culture tank 22. Alternatively, as illustrated in FIG. 3E, a cover 6 that can be arranged on the first culture medium supply hole 221 side of the first base material 21 may be provided, and the one end 231 of the pillar 23 may be formed to the cover 6, and thereby the other end 232 of the pillar 23 may be arranged in the first culture tank 22 when covered. Further, although the example in which the two pillars 23 are arranged is illustrated in the example of FIG. 3A to FIG. 3D, a single pillar 23 may be formed, and a skeletal muscle tissue may be formed between the single pillar 23 and the other end part 44 of the third unit 4 (a portion corresponding to a virtual axon channel 42a of FIG. 3D).

Further, although the embodiment of the pillar 23 described above illustrates an example in which the one end 231 of the pillar 23 is formed to the first base material 21 or the cover 6 such that the other end 232 of the pillar 23 is arranged in the first culture tank 22, the arrangement and the number of pillars 23 are not particularly limited as long as a skeletal muscle tissue can be formed. For example, as illustrated in FIG. 3F, both ends of substantially a U-shaped single pillar 23 may be attached to the cover 6. Further, as illustrated in FIG. 3G, both ends of substantially a U-shaped single pillar 23 may be attached to the side wall surface 212 of the first base material 21. Alternatively, as illustrated in FIG. 3H, both ends of each of the two pillars 23 may be connected to the first base material 21 so as to traverse the first culture tank 22. When the pillars 23 are formed of a flexible material, the pillars 23 can be warped in accordance with contraction of a skeletal muscle tissue formed between the pillars 23 also in the example illustrated in FIG. 3F to FIG. 3H.

Further, when the pillar 23 is formed in a cantilevered manner, although not illustrated, the other end 232 of the pillar 23 may be larger than the remaining portion, if necessary. Because the other end 232 is larger than the remaining portion, the formed skeletal muscle tissue is less likely to be come off of the pillar 23.

Although the first base material 21 and the first culture tank 22 are formed in substantially a rectangular parallelepiped shape in the example illustrated in FIG. 3A and FIG. 3D, the shapes of the first base material 21 and the first culture tank 22 are not particularly limited as long as the first culture tank 22 is formed in the first base material 21. Further, the shape of the pillar 23 is also not particularly limited as long as a skeletal muscle tissue can be formed and may be, for example, a cylindrical shape, a polygonal prism shape, or the like.

Although a cut-off 24 used for placing the second unit 3 described later is formed in the first base material 21 in the example illustrated in FIG. 3A and FIG. 3D, the formation of the cut-off 24 is not essential as described later.

The first base material 21 and the pillar 23 or the cover 6 and the pillar 23 may be integrally formed or separately formed. When separately formed, the pillar 23 can be adhered to the wall surface of the first base material 21 or to the cover 6. Further, when the other end 232 of the pillar 23 is formed larger, the pillar 23 may be formed in advance with the large other end 232, or a separate member may be attached to the other end 232 of the pillar 23 to have a larger pillar 23.

The forming method of the first base material 21 and the pillar 23 (and cut-off 24 if necessary) may be not particularly limited. For example, formation by preparing a material used for forming the first base material 21 and cutting the material, formation by using a 3D printer, or the like may be employed. Further, a mold is first fabricated by using a photolithography technology, and a material used for forming the first base material 21 may then be transferred. Note that when the mold is transferred for fabrication, a plurality of molds may be used as required to fabricate components of the first unit 2, and these components may be combined to fabricate the first unit 2.

When the first base material 21 and the pillar 23 are fabricated by a method of cutting or mold transfer, the material is not particularly limited as long as it can be used for cutting or mold transfer. The material may be, for example, a thermoplastic resin such as polyethylene, polypropylene, polyvinyl chloride, polyvinylidene chloride, polystyrene, polyvinyl acetate, polytetrafluoroethylene, an acrylonitrile butadiene styrene (ABS) resin, an acrylonitrile styrene (AS) resin, a fluorine resin such as Teflon (registered trademark), or an acrylic resin (PMMA); or a thermosetting resin such as a phenol resin, an epoxy resin, a melamine resin, a urea resin, an unsaturated polyester resin, an alkyd resin, polyurethane, thermosetting polyimide, or a silicon rubber or the like. Note that, when a skeletal muscle tissue formed in the first unit 2 is stained and observed, a light transmitting resin is desirable. The resin in such a case may be, for example, a plastic made of a cyclo-olefin polymer (COP), polydimethylsiloxane (PDMS), polymethylmeth-acrylate (PMMA), polycarbonate (PC), rigid polyethylene, or the like, a silicon resin, or the like. Further, instead of a resin, a metal may be used. Note that, when the pillar 23 is formed in the cover, this can be fabricated by the same material and the same manufacturing method as the first base material 21.

Further, when a 3D printer is used for fabrication, a molding resin commercially available for 3D printers can be used.

Next, the second unit 3 will be described in more detail with reference to FIG. 3B to FIG. 3D. In the example illustrated in FIG. 3B to FIG. 3D, the second unit 3 includes a second base material 31, a second culture tank 32, and a third unit insertion part 33 in which one end part 43 of the third unit 4 is inserted. The second culture tank 32 is used for culturing motor neurons and extending axons from cell bodies of the cultured motor neurons. The second culture tank 32 is formed in the second base material 31 and, in the example illustrated in FIG. 3C and FIG. 3D, formed in substantially a recess shape having a second culture medium supply hole 321 in the upper face of substantially the rectangular parallelepiped second base material 31.

In the example illustrated in FIG. 3B, an axon channel opening 421 is formed in a side surface 431 of the one end part 43 of the third unit. Therefore, when the one end part 43 of the third unit 4 is inserted in the third unit insertion part 33, the axon channel opening 421 of an axon channel 42 communicates with the second culture tank 32. Thus, the axon extending from the cell body of the motor neuron cultured in the second culture tank 32 can pass through the axon channel 42 and extend in the direction of the first unit 2. Note that an axon is a part of a motor neuron but may be simply referred to as "axon" below when description is provided focusing on an axon portion.

Figures 4A, 4B, 4C:
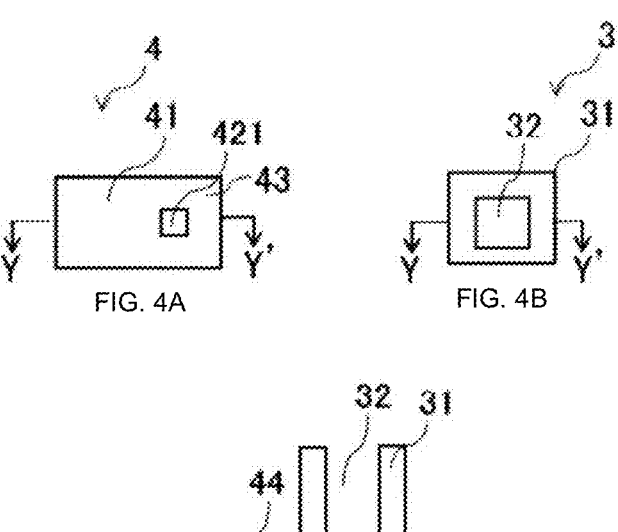

Note that, although FIG. 3B to FIG. 3D illustrate the example in which the third unit insertion part 33 is formed in the second unit 3, the connection between the second unit 3 and the one end part 43 of the third unit 4 may be in another form as long as the axon channel 42 and the second culture tank 32 communicate with each other. FIG. 4A to FIG. 4C are diagrams illustrating an example of other embodiments for the connection between the second unit 3 and the one end part 43 of the third unit 4. FIG. 4A is a top view (a diagram viewed from the R1 direction of FIG. 3B) of the third unit 4, FIG. 4B is a top view (a diagram viewed from the R1 direction of FIG. 3C) of the second unit 3, and FIG. 4C is a schematic sectional view (a diagram taken along the direction Y-Y' of FIG. 4A and FIG. 4B) when the second unit 3 is overlapped with the top surface of the third unit 4.

In the example illustrated in FIG. 4A to FIG. 4C, the second culture tank 32 is formed so as to penetrate the second base material 31. Further, unlike the example illustrated in FIG. 3B, the axon channel opening 421 is formed so as to penetrate the top surface of the third base material 41 of the one end part 43 of the third unit. Therefore, with connection being made such that the second culture tank 32 of the second unit 3 overlaps the axon channel opening 421, the axon channel 42 and the second culture tank 32 can communicate with each other. Note that, in the example illustrated in FIG. 4A to FIG. 4C, it is desirable that an axon extending from a cell body of the motor neuron cultured in the second culture tank 32 pass through the axon channel opening 421 and extend only to the other end part 44 (on the side arranged to the first unit 2) of the third unit. Therefore, as illustrated in FIG. 4C, no channel may be formed in a portion of the one end part 43 of the third unit 4 in the direction of the side surface 431 from the axon channel opening 421. Further, as is clear from the above description, in the present specification, the "one end part 43" of the third unit 4 means a portion inserted in the second unit 3 or overlapped with the second unit 3.

Although the second base material 31 and the second culture tank 32 are formed in substantially a rectangular parallelepiped shape in the example illustrated in FIG. 3C and FIG. 3D and FIG. 4A to FIG. 4C, the shapes of the second base material 31 and the second culture tank 32 are not particularly limited as long as the second culture tank 32 is formed in the second base material 31. Further, the fabrication and the material of the second unit 3 can be the same as those for the first unit 2.

Next, the third unit 4 will be described in more detail with reference to FIG. 3B and FIG. 3D and FIG. 5A and FIG. 5B. FIG. 5A is a sectional view in the direction Z-Z' of FIG. 3B, and FIG. 5B is a sectional view in the direction a-a' of FIG. 5A, which is a schematic sectional view illustrating the structure in more detail of the other end part 44 of the third unit 4. In the example illustrated in FIG. 3B and FIG. 3D, the third unit 4 includes the third base material 41 and the axon channel 42. The third unit 4 includes the one end part 43, which is a portion inserted in the second unit 3 or overlapped with the second unit 3, and the other end part 44, which is arranged on the opposite side from the one end part 43 and faces the first unit 2. Further, a first opening part 45 is formed to the other end part 44 so as to be in contact with the axon channel 42.

One or more first axon passage holes 451 are formed in the first opening part 45. The number of first axon passage holes 451 is not particularly limited as long as it is greater than or equal to one and may be two or greater, three or greater, four or greater, or the like, which can be suitably determined taking the size of the third unit 4 or the like into consideration. Each first axon passage hole 451 has a size that is smaller than the sectional area of the axon channel 42 and through which at least one axon extending from the inside of the axon channel 42 can pass but neither a motor neuron nor a skeletal muscle cell can pass. Note that, in the present specification, the "sectional area" of the axon channel 42 means the size of a plane orthogonal to the direction in which an axon extends (the direction toward the first opening part 45, the arrow direction in FIG. 5A). Further, the size of the first axon passage hole 451 means the size of a first opening face 451a of the first axon passage hole 451 on the axon channel 42 side or a second opening face 451b on the opposite side from the first opening face 451a.

The first opening face 451a and the second opening face 451b will be described in more detail with reference to FIG. 6. FIG. 6A is a diagram illustrating the shape of the first opening face 451a or the second opening face 451b. Further, FIG. 6B is a diagram illustrating the size of the first opening face 451a and the second opening face 451b. As described above, the first axon passage hole 451 is required to have a size through which neither a motor neuron nor a skeletal muscle cell can pass but at least one axon can pass, however, the shape or the like of the first axon passage hole 451 is not particularly limited as long as the size is ensured. The first axon passage hole 451 may have a columnar structure such as a cylinder, an elliptic cylinder, a triangular prism, a rectangular prism, or the like, for example, in other words, may be a cylindrical member in which the first opening face 451*a* and the second opening face 451*b* have the same shape and the same size. Further, the first axon passage hole 451 may be a part of a pyramid such as a cone, a triangular pyramid, a quadrangular pyramid, in other words, may be a cylindrical member in which at least one of the shape and the size is different between the first opening face 451*a* and the second opening face 451*b*.

As illustrated in FIG. 6A, the shape of the first opening face 451*a* and the second opening face 451*b* may be a circle, an ellipse, a polygon, or the like and is not particularly limited. Note that, in the present specification, the definition when referring to "size" of the first opening face 451*a* and the second opening face 451*b* will be described with reference to FIG. 6B. When the shape of the first opening face 451*a* and the second opening face 451*b* is a circle, the "size" represents the diameter. On the other hand, the size is not uniquely determined in a case of a shape other than a circle, for example, an ellipse or a polygon or a shape combining one or more curves and one or more straight lines. Thus, as illustrated in FIG. 6B, out of a plurality of distances d obtained when the first opening face 451*a* (second opening face 451*b*) is interposed between parallel lines, the shortest distance d is defined as "minimum distance", and out of the plurality of distances d, the longest distance d is defined as "maximum distance". When the shape of the first opening face 451*a* and the second opening face 451*b* is a circle, the "minimum distance" and the "maximum distance" are the same.

The first opening face 451*a* that may be infiltrated with motor neurons is required to have a size that does not pass a motor neuron. While varying in accordance with culture conditions or the like, a motor neuron is a non-spherical cell having a size of approximately 5 μm to 30 μm. Further, a motor neuron deforms to some extent. Therefore, if the "minimum distance" of the first opening face 451*a* is a size less than 2.5 μm, less than or equal to 2.0 μm, or the like, for example, a motor neuron does not deform so as to be smaller than the above "minimum distance". Therefore, when the "minimum distance" is less than 2.5 μm, for example, the "maximum distance" is not particularly limited.

On the other hand, if the "minimum distance" is a certain size, for example, greater than or equal to 2.5 μm, it is required to take into consideration of not only the "minimum distance" but also the sectional area (sectional shape) of the first opening face 451*a* in terms of whether or not a motor neuron passes therethrough. For example, if no motor neuron passes when the sectional area is 60 μm², suitable adjustment can be made such that the "maximum distance" is less than or equal to 24 μm when the "minimum distance" is 2.5 μm, the "maximum distance" is less than or equal to 20 μm when the "minimum distance" is 3 μm, the "maximum distance" is less than or equal to 15 μm when the "minimum distance" is 4 μm, the "maximum distance" is less than or equal to 12 μm when the "minimum distance" is 5 μm, the "maximum distance" is less than or equal to 10 μm when the "minimum distance" is 6 μm, or the like.

Note that the example of the sectional area described above is a value found from a general size of motor neurons, and the sectional area is not limited to 60 μm². The sectional area may be suitably changed to, for example, 58 μm² or less, 56 μm² or less, 54 μm² or less, 52 μm² or less, 50 μm² or less, or the like.

Similarly, the second opening face 451*b* that may be infiltrated with skeletal muscle cells is required to have a size through which a skeletal muscle cell is unable to pass. The size of a skeletal muscle cell is approximately 5 μm to 30 μm as with a motor neuron. Therefore, the size of the second opening face 451*b* can be adjusted to be the same "minimum distance" or "sectional area" as the first opening face 451*a*.

Further, in order for at least one axon to pass, a distance of approximately 0.5 μm is required. Therefore, the "minimum distance" of the first opening face 451*a* and the second opening face 451*b* can be greater than or equal to 0.5 μm, greater than or equal to 1 μm, greater than or equal to 1.5 μm, or greater than or equal to 2 μm.

Further, the length of the first axon passage hole 451 (the distance between the first opening face 451*a* and the second opening face 451*b*) is not particularly limited in terms of passage of an axon. The length can be suitably determined in terms of convenience in manufacturing, convenience in handling, or the like. The lower limit may be, for example, greater than or equal to 1 μm, greater than or equal to 50 μm, or greater than or equal to 100 μm. Further, the upper limit may be, for example, less than or equal to 1000 μm, less than or equal to 750 μm, or less than or equal to 500 μm.

The shape or the size of the axon channel 42 is not particularly limited as long as the periphery thereof is covered with the third base material 41 (there may be an uncovered part in the case of the example illustrated in FIG. 4), the first opening part 45 is formed to the other end part 44, and the one end part 43 can communicate with the second culture tank 32. As illustrated in FIG. 3B, the sectional shape may be substantially a rectangle or may be a polygon or a circle. Further, the width of the axon channel 42 (the length in a direction substantially orthogonal to a line connecting the one end part 43 to the other end part 44) is not particularly limited. For example, the width of the axon channel 42 may be 10 μm to 1000 μm, 100 μm to 750 μm, or 250 μm to 500 μm. Further, the height of the axon channel 42 (the length in the perpendicular direction in FIG. 3B) may be 10 μm to 200 μm, 30 μm to 100 μm, or 50 μm to 75 μm.

Note that, if both of the width and the height of the axon channel 42 are sufficiently larger than a motor neuron, a motor neuron may enter the axon channel 42. In such a case, a slit for preventing passage of a motor neuron may be provided to a junction portion of the second culture tank 32 and the axon channel 42 or the axon channel 42. More specifically, for example, as illustrated in FIG. 4C, if the second unit 3 is overlapped on the third unit 4, the size of the axon channel opening 421 may be required to be a size through which a motor neuron is unable to pass. Note that, although the size of the axon channel opening 421 is adjusted in the example illustrated in FIG. 4C, alternatively, a hole may be formed in the bottom of the second culture tank 32 to perform adjustment by the size of the hole. Alternatively, as illustrated in FIG. 5A, a slit 423 having a size through which a motor neuron does not pass may be formed at a position spaced apart from the first opening part 45 of the axon channel 42.

Although the first axon passage holes 451 are arranged laterally in a line in the example illustrated in FIG. 5B, two lines of the first axon passage holes 451 may be arranged as illustrated in FIG. 5C. Alternatively, although depiction is omitted, three or more lines of first axon passage holes 451 may be arranged. Further, although the example in which the first opening part 45 and the axon channel 42 are fabricated as separated members is illustrated in the example of FIG. 5, the first opening part 45 and the axon channel 42 may be integrally fabricated. Further, the fabrication and the mate- rial of the third unit may be the same as those of the first unit 2.

The device 1*a* according to the first embodiment may be provided with the first to third units being separated or may be provided with the first to third units being combined. Further, when the pillars 23 are provided to the cover 6, the device 1*a* may be provided with the cover 6 being separated. FIG. 3D illustrates an example of a positional relationship when the first to third units are combined. An axon extend- ing from the first axon passage hole 451 of the first opening part 45 of the third unit 4 to the inside of the first culture tank 22 reaches a skeletal muscle tissue formed between the pillars (for example, between the other ends 232) to make a neuromuscular junction. It is thus desirable that the third unit 4 be arranged so that an axon easily reaches a skeletal muscle tissue. In the example illustrated in FIG. 3D, a virtual axon channel 42*a* that is a virtually extended axon channel 42 in the first culture tank 22 is arranged so as to cross any of extension lines connecting the other ends 232 of two or more pillars 23 to each other (alternatively, virtual planes connecting two or more pillars 23 to each other). The skeletal muscle tissue is organized on the pillars 23 as a scaffold so as to be connected between the pillars 23. Therefore, with the other end part 44 of the third unit 4 and the first unit 2 being arranged as described above, this facilitates formation of a neuromuscular junction. Further, as illustrated in FIG. 3F and FIG. 3G, when a single pillar 23 is provided, it is desirable to have arrangement such that the virtual plane formed by the single pillar 23 intersects the virtual axon channel 42*a*. Further, when forming the skeletal muscle tissue by using the single pillar 23 and the other end part of the third unit 4, it is desirable to have arrangement such that the virtual plane formed by the single pillar 23 and the other end part of the third unit 4 intersects the virtual axon channel 42*a*.

Note that, in the example illustrated in FIG. 3D, the third device 4 is connected in a direction substantially orthogonal to the gravity direction of the second culture tank 32. Thus, to cause the virtually extended virtual axon channel 42*a* to intersect the direction of a skeletal muscle tissue formed floating in a culture medium described later, it is preferable to form the cut-off 24 used for arranging the second unit 3 in the first unit 2. On the other hand, when the third device 4 is connected to the second device 3 with inclination so that the other end part 44 of the third unit 4 is on the lower side in the gravity direction, this enables arrangement such that the virtually extended virtual axon channel 42*a* intersects any of the virtual planes formed by two or more pillars 23 even when the bottom of the second device 3 is placed on the top surface of the first base material 21 of the first device 2. Therefore, the cut-off 24 can be formed when required.

[Second Embodiment of Device]

Figures 7A, 7B:
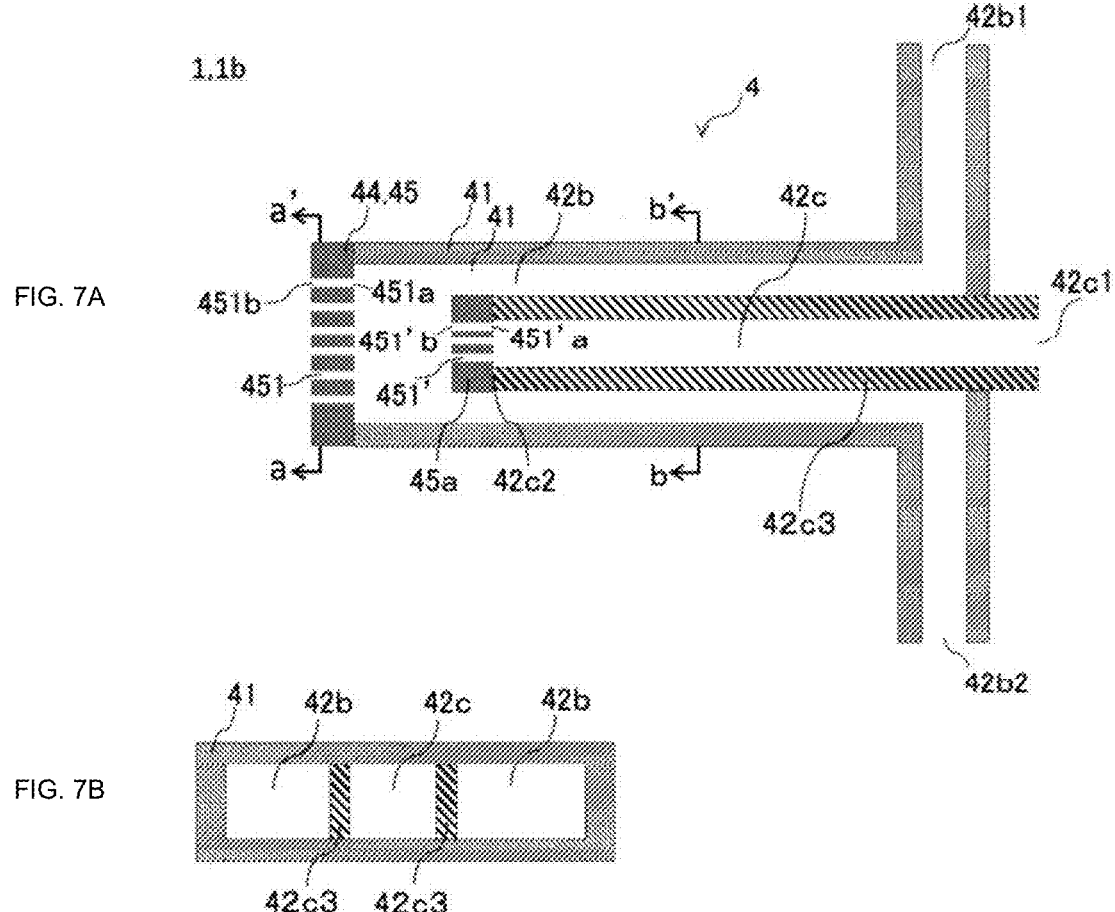
FIG. 7A and FIG. 7B are schematic sectional views illustrating a device 1b according to a second embodiment.

Next, a device 1*b* according to a second embodiment will be described with reference to FIG. 7A and FIG. 7B. FIG. 7A is a schematic sectional view of the device 1*b* of the second embodiment (in the same direction as in FIG. 5A), and FIG. 7B is a sectional view taken along a line b-b' of FIG. 7A. The device 1*b* according to the second embodiment differs from the device 1*a* according to the first embodiment in that a channel is further formed inside the axon channel 42 of the third unit 4, however, other features are the same as those of the device 1*a* according to the first embodiment.

Therefore, in the second embodiment, features different from those of the first embodiment will be mainly described, and duplicated description for the features already described in the first embodiment will be omitted. Thus, needless to say, the feature already described in the first embodiment can be employed in the second embodiment even when not explicitly described in the second embodiment.

The axon channel 42 illustrated in FIG. 7A includes a first channel 42*b* and a second channel 42*c* formed inside the first channel 42*b*. The first opening part 45 is formed so as to be in contact with the first channel 42*b*. One end 42*c*1 of the second channel 42*c* communicates with the second culture tank 32, and a second opening part 45*a* is formed to and in contact with the other end 42*c*2 of the second channel 42*c*. One or more second axon passage holes 451' are formed in the second opening part 45*a*. The second axon passage hole 451' has a size through which neither a motor neuron nor a skeletal muscle cell can pass but an axon can pass. Further, the first opening part 45 and the second opening part 45*a* are arranged spaced apart from each other. Thus, an axon extending from a cell body of a motor neuron cultured in the second culture tank 32 passes through the second opening part 45*a*, then passes through the first channel 42*b*, further passes through the first opening part 45, and forms a neuromuscular junction with a skeletal muscle tissue. On the other hand, the one end 42*b*1 and the other end 42*b*2 of the first channel 42*b* do not communicate with the second culture tank 32. Therefore, since the first channel 42*b* is not infiltrated with motor neurons or skeletal muscle cells, it is possible to selectively stimulate only axons by pouring, into the first channel 42*b*, a culture medium mixed with a test substance of a therapeutic agent against a neuromuscular disease.

In the example illustrated in FIG. 7A, "second axon passage hole 451'" may be replaced with "first axon passage hole 451", "first opening face 451*a*'" may be replaced with "first opening face 451", and "second opening face 451*b*'" may be replaced with "second opening face 451*b*". In other words, while the second opening part 45*a* has a smaller size than the first opening part 45, an axon passage hole, a first opening face, and a second opening face formed in the first opening part 45 and the second opening part 45*a* may have the same shape and the same size. The axon passage hole, the first opening face, and the second opening face formed in the first opening part 45 and the second opening part 45*a* may have different shapes and different sizes as long as they are within the shapes and the sizes of the axon passage hole, the first opening face, and the second opening face described in the first embodiment.

The device 1*b*, more specifically, the third unit 4 accord- ing to the second embodiment can be such that a second channel wall surface 42*c*3 is formed inside the first channel 42*b* by using the same material as the third base material 41, as illustrated in FIG. 7B. Further, the fabrication and the material of the third unit 4 of the device 1*b* according to the second embodiment may be the same as the third unit 4 of the device 1*a* according to the first embodiment.

[Third Embodiment of Device]

Figure 8A:
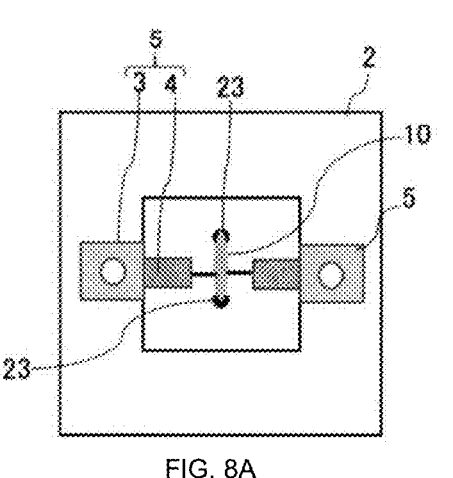
FIG. 8A and FIG. 8B are schematic top views illustrating a device 1c according to a third embodiment.
Figure 8B:
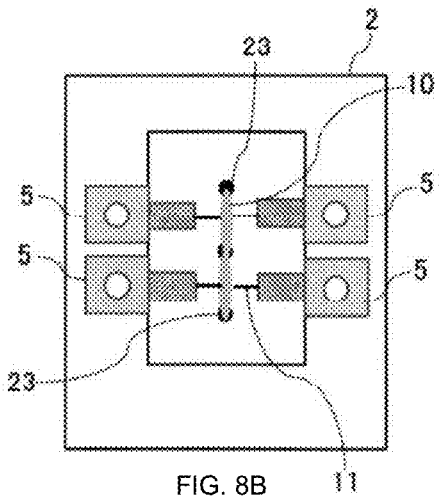

Next, a device 1*c* according to a third embodiment will be described with reference to FIG. 8A and FIG. 8B. FIG. 8A and FIG. 8B are schematic top views of the device 1*c* according to the third embodiment. The device 1*c* according to the third embodiment differs from the device 1*a* according to the first embodiment and the device 1*b* according to the second embodiment in that the second unit 3 and the third unit 4 are connected to fabricate a motor neuron culturing device 5 and two or more motor neuron culturing devices 5 are arranged for one first unit 2, however, other features are the same as those of the device 1*a* according to the first embodiment and the device 1*b* according to the second embodiment. Therefore, in the third embodiment, features different from those of the first embodiment and the second embodiment will be mainly described, and duplicated description for the features already described in the first embodiment and the second embodiment will be omitted. Thus, needless to say, the feature already described in the first embodiment and the second embodiment can be employed in the third embodiment even when not explicitly described in the third embodiment.

FIG. 8A illustrates an example in which two motor neuron culturing devices 5 are arranged for the single skeletal muscle tissue formed between two pillars 23 and a neuromuscular junction is formed of the axons 11 extending from respective motor neuron culturing devices 5 and the skeletal muscle tissue 10. In the example illustrated in FIG. 8A, two axons 11 are connected to the single skeletal muscle tissue. Therefore, in screening of a therapeutic agent against a neuromuscular disease, it is possible to change the type of the test substance supplied to respective motor neuron culturing devices 5 or observe the effect when the concentration is changed for the same type of the test substance. Note that, although the example in which the two motor neuron culturing devices 5 are arranged is illustrated in the example of FIG. 8A, three or more motor neuron culturing devices 5 may be arranged as long as the axons 11 extending from the motor neuron culturing devices 5 can form a neuromuscular junction with the skeletal muscle tissue 10.

FIG. 8B illustrates an example in which two motor neuron culturing devices 5 are arranged for each of skeletal muscle tissues formed between three pillars 23, respectively, and neuromuscular junctions are formed of the axons 11 extending from respective motor neuron culturing devices 5 and the skeletal muscle tissues 10. Also in the example illustrated in FIG. 8B, screening of a plurality of test substances can be implemented at the same time in the same manner as in the example illustrated in FIG. 8A. Further, also in the example illustrated in FIG. 8B, three or more motor neuron culturing devices 5 may be arranged for the skeletal muscle tissue 10 at a single position. Note that, in the example illustrated in FIG. 8B, for example, when one of the skeletal muscle tissues 10 is stimulated and contracted, the other skeletal muscle tissue 10 can be expanded. Since muscles work in pairs in organisms, a phenomenon closer to an organism can be reproduced in the example illustrated in FIG. 8B.

[Fourth Embodiment of Device]

Figure 9A:
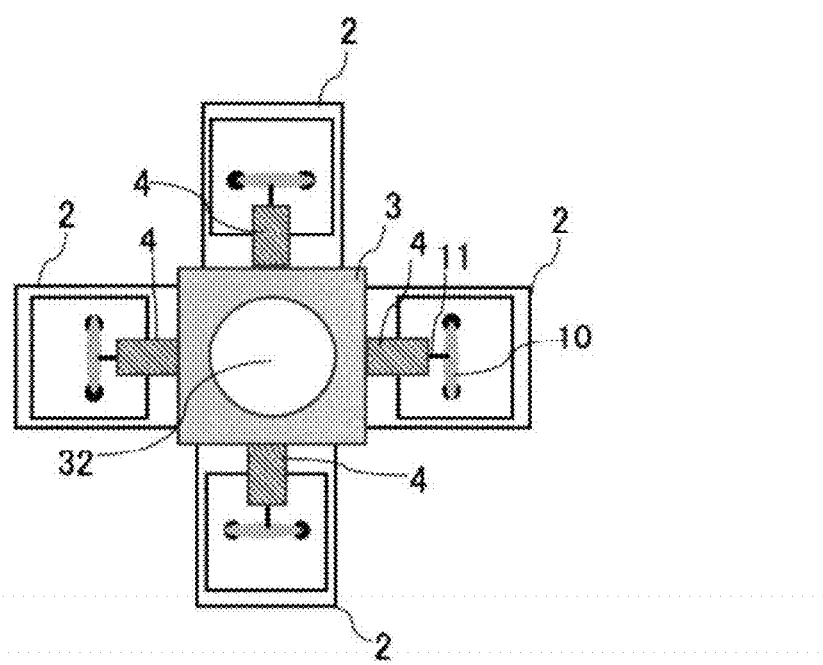
FIG. 9A is a schematic top view illustrating a device 1d according to a fourth embodiment.

Next, a device 1*d* according to a fourth embodiment will be described with reference to FIG. 9A. FIG. 9A is a schematic top view of the device 1*d* according to the fourth embodiment. The device 1*d* according to the fourth embodiment differs from the device 1*a* according to the first embodiment and the device 1*b* according to the second embodiment in that two or more third units 4 are connected to one second unit 3 to fabricate a motor neuron culturing device 5*a* and the first unit 2 is arranged to the other end of each third unit 4, however, other features are the same as those of the device 1*a* according to the first embodiment and the device 1*b* according to the second embodiment. Therefore, in the fourth embodiment, features different from those of the first embodiment and the second embodiment will be mainly described, and duplicated description for the features already described in the first embodiment and the second embodiment will be omitted. Thus, needless to say, the feature already described in the first embodiment and the second embodiment can be employed in the fourth embodiment even when not explicitly described in the fourth embodiment.

In the device 1*d* according to the fourth embodiment, the axon 11 extending from a cell body of a motor neuron cultured by the one second unit 3 can be joined to different skeletal muscle tissues 10 to form neuromuscular junctions. Also when one first unit 2 and one second unit 3 are provided, it is possible to fabricate an evaluation model to screen a test substance of a therapeutic agent against a neuromuscular disease. However, for example, when formation of the skeletal muscle tissue from skeletal muscle cells is insufficient or formation of the neuromuscular junction is insufficient, even a useful test substance may be missed in screening. On the other hand, in the device 1*d* according to the fourth embodiment, the axon 11 extending from a clump of motor neurons cultured in the second culture tank 32 can form neuromuscular junctions with different skeletal muscle tissues. Therefore, for example, when performing screening of test substances of a therapeutic agent against a neuromuscular disease that stimulates motor neurons, it is possible to confirm whether or not the skeletal muscle tissue 10 moves in the same manner, and it is thus possible to improve accuracy in screening of a test substance.

The first to fourth embodiments described above illustrate examples of the device 1 disclosed in the present specification, and the present invention is not limited to the embodiments described above. Any combination of respective embodiments described above or modification of any component or omission of any component of each embodiment is possible. For example, although the third unit 4 is in the single-layer structure in which the third base material 41 covers the periphery of the axon channel 42 in the first to fourth embodiments, the third units 4 may be stacked to form a multi-layer structure. When the multi-layer structure is employed, since the axon extending from the first opening part 45 to the skeletal muscle tissue 10 becomes three-dimensional, this facilitates formation of a neuromuscular junction.

[Embodiment of Motor Neuron Culturing Device]

The motor neuron culturing device 5 has already been described in the third and fourth embodiments for the device 1. Thus, description of the motor neuron culturing device 5 will be omitted for avoiding duplicated description. Note that, when the second unit 3 and the third unit 4 are combined to provide the motor neuron culturing device 5, the second unit 3 and the third unit 4 may be integrated or components common to the second unit 3 and the third unit 4 may be used in combination to fabricate the motor neuron culturing device 5. For example, a part of the second base material 31 and the third base material 41 may be formed of a single component.

In the third and fourth embodiments, the example to fabricate the co-culturing device 1 by combining the motor neuron culturing device 5 with the first unit 2 has been described. Alternatively, when the third unit 4 includes the first channel 42*b* and the second channel 42*c* formed inside the first channel 42*b* as illustrated in FIG. 7A, the motor neuron culturing device 5 may be used alone as a modeling device that reproduces rupture and reproduction of an axon. For example, a clinical condition referred to as neuropathies in which the normal conduction of peripheral nerves is impaired is known. Further, among neuropathies, a traumatic neuropathy and an axonal degeneration neuropathy due to local axotomy are known. As illustrated in Examples described later, application to an axonal degeneration neuropathy model can be expected, which is resulted by rupturing an axon between the second opening part 45*a* of the second channel 42*c* and the first opening part 45 of the first channel 42*b* of the motor neuron culturing device 5 by application of a shear stress or the like and then reproducing the axon. Note that the model that reproduces rupture and reproduction of an axon may also be fabricated by using a co-culturing device 1.

[Embodiment of Multi-Well Plate]

Figure 9B:
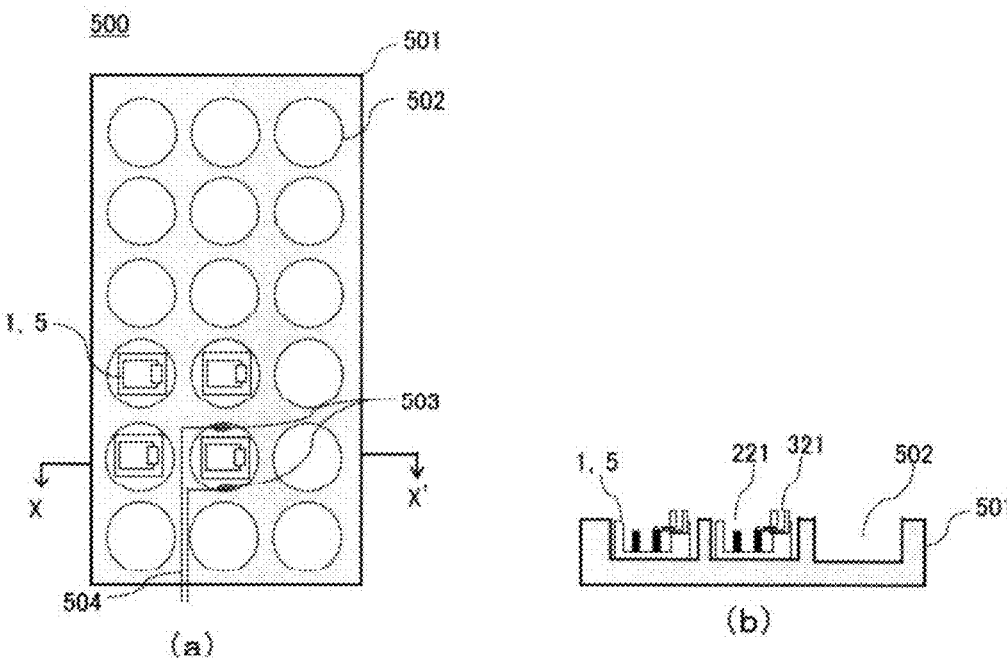
FIG. 9B (a) and (b) are diagrams illustrating an overview of an embodiment of a multi-well plate.

A multi-well plate 500 will be described with reference to FIG. 9B. FIG. 9B(a) is a top view illustrating the overview of the multi-well plate 500, and FIG. 9B(b) is a sectional view taken along a line X-X' of FIG. 9B(a). The multi-well plate 500 has a base material 501 and at least two or more wells 502 formed on the base material 501. Further, a device selected from the device 1 described in the first to fourth embodiments and the motor neuron culturing device 5 is arranged in at least one well 502. Further, if necessary, a pair of electrodes 503 may be formed in any of the wells 502. Further, a circuit 504 for connecting the pair of electrodes 503 to a power supply apparatus (not illustrated) may be formed on the base material 501.

In the multi-well plate 500, the number or the shape of wells 502 is not particularly limited as long as the device 1 or 5 can be arranged in the well 502. Although the well 502 is formed in substantially a cylindrical shape in the substrate 501 in the example illustrated in FIG. 9B, the shape may be, for example, a hemisphere, substantially a polygonal prism, or the like.

The devices 1 or 5 arranged in the wells 502 may all be of the same type or may be of different types in combination. Further, the devices 1 or 5 may be arranged in some of the wells 502 or may be arranged in all of the wells 502. Each of the devices 1 or 5 may be arranged in the well 502 in a detachable manner, in other words, may be only inserted in the well 502 or may be arranged in a non-detachable manner. When arranged in a non-detachable manner, each of the devices 1 or 5 can be fixed to the wall surface of the well 502 by using an adhesive agent or the like.

With the devices 1 or 5 being arranged in wells, the following advantageous effects are synergetically achieved.

(1) When a culture medium is supplied to the first culture medium supply hole 221 or the second culture medium supply hole 321, even if the culture medium overflows from the first culture tank or the second culture tank, the culture medium remains in the well 502, and thus, convenience in adding a culture medium is improved.

(2) With the devices 1 or 5 being arranged on the multi-well plate, this enables simultaneous assay or screening of a plurality of drugs or the like and enables a higher throughput. Note that, in the example illustrated in FIG. 9B, since the devices 1 or 5 are arranged in the wells 502, the above advantageous effect of (1) and a higher throughput of a drug assay or the like can be achieved at the same time. Alternatively, when a higher throughput of a drug assay or the like is focused on, the devices 1 or 5 may be arranged on a plate-like member having no well, such as a glass substrate, instead of the multi-well plate.

(3) Further, when the pair of electrodes 503 are arranged in the well 502, it is also possible to electrically stimulate a fabricated evaluation model. Note that, although the example in which the pair of electrodes 503 are provided to the well 502 is illustrated in the example of FIG. 9B, alternatively, a pair of electrodes may be provided to the inner wall surface of the culture tank or the like of the device 1 or 5. Further alternatively, only when it is intended to electrically stimulate an evaluation model, a pair of electrodes may be inserted to the well 502 of the well plate 500 or the culture tank or the like of the device 1 or 5 to electrically stimulate the evaluation model.

[Embodiment of Fabrication Method of Evaluation Model]

Figure 10:
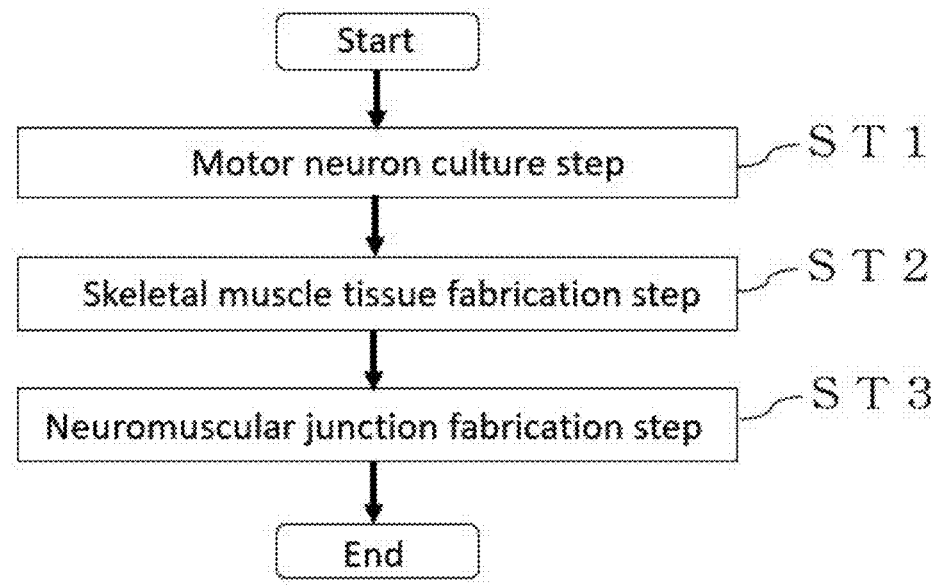
FIG. 10 is a flowchart of an embodiment of a fabrication method of an evaluation model.

Next, an embodiment of a fabrication method of an evaluation model will be described with reference to FIG. 10. The embodiment of the fabrication method of an evaluation model is implemented by using the device 1 described above. FIG. 10 is a flowchart of the embodiment of the fabrication method of an evaluation model. The embodiment of the fabrication method of an evaluation model includes a motor neuron culture step (ST1), a skeletal muscle tissue fabrication step (ST2), and a neuromuscular junction fabrication step (ST3).

In the motor neuron culture step (ST1), motor neurons are cultured in the second culture tank 32 of the second unit 3. The motor neuron is not particularly limited as long as, when cultured, it can extend the axon 11. For example, the motor neuron disclosed in Non-Patent Literature 1 or Non-Patent Literature 2 can be used. Further, motor neurons may be cultured from separate motor neurons in the second culture tank 32, or a spheroid that is a clump of motor neurons may be used. Further, the culture medium used for culturing the motor neurons may be suitably selected in accordance with motor neurons to be used.

In the skeletal muscle tissue fabrication step (ST2), skeletal muscle cells are cultured in the first culture tank 22 of the first unit 2 to fabricate a skeletal muscle tissue. The skeletal muscle cell is not particularly limited as long as, when cultured, it can form the skeletal muscle tissue 10 between the pillars 23. Also for the skeletal muscle cell, the skeletal muscle cell disclosed in Non-Patent Literature 1 or Non-Patent Literature 2 can be used, for example. Further, the culture medium used for culturing the skeletal muscle cells may be suitably selected in accordance with skeletal muscle cells to be used. Note that the motor neuron culture step (ST1) and the skeletal muscle tissue fabrication step (ST2) may be performed in the opposite order or may be performed simultaneously.

In the neuromuscular junction fabrication step (ST3), the axon 11 extending from a cell body of the cultured motor neuron passes through the axon channel 42 of the third unit 4 and joins to the skeletal muscle tissue fabricated in the first culture tank 22, and thereby a neuromuscular junction is fabricated. With the above step, the skeletal muscle tissue and the cell body of the motor neuron can be joined by the axon 11 in a state where the skeletal muscle tissue is floating in the culture medium and a state where the skeletal muscle tissue and the cell body of the motor neuron are separated, and therefore, an evaluation model closer to the actual human body can be fabricated.

The device 1 disclosed in the present specification uses a culture medium in culturing motor neurons and skeletal muscle cells. Therefore, the culture medium can be infiltrated, by capillary force, into the axon channel 42 of the third device 4 and the first axon passage holes 451 (second axon passage holes 451') that is smaller than the axon channel 42. On the other hand, the device (fabrication method of the evaluation model) disclosed in Non-Patent Literature 2 uses collagen gel as a scaffold for extending an axon, however, such collagen gel has viscosity. Therefore, if the channel through which an axon extends is simply thinned in the invention disclosed in Non-Patent Literature 2, this will prevent the collagen gel containing a culture medium from being infiltrated into the channel. The device 1 and the fabrication method of the evaluation model using the device 1 disclosed in the present specification are based on a novel finding that the axon channel 42 and the first axon passage holes 451 (second axon passage holes 451') are used as a scaffold on which the axon 11 extends and, furthermore, a culture medium infiltrating into the scaffold is combined.

Furthermore, the evaluation model fabricated with the device 1 disclosed in the present specification does not use collagen as a scaffold and thus achieves the following combined advantageous effects in addition to the advantageous effect of easier observation of movement of a skeletal muscle tissue or the like.

(1) If a scaffold is formed of collagen gel, to stimulate a motor neuron, an axon, and a skeletal muscle tissue by using a drug, it is required for the drug to infiltrate into the collagen gel. This will therefore prevent quick screening of the drug. Further, the drug is dispersed when infiltrated into the collagen gel, and this will make it difficult to perform screening specifying a target of a motor neuron, an axon extending from a cell body of the motor neuron, or a skeletal muscle tissue.

On the other hand, the evaluation model fabricated with the device 1 disclosed in the present specification enables a state where a motor neuron, a skeletal muscle tissue, and an axon extending from a cell body of the motor neuron are separated. Therefore, this makes it possible to narrow down a target and perform screening of a drug. Further, since a motor neuron, a skeletal muscle tissue, and an axon extending from a cell body of the motor neuron are formed in culture media, respectively, this enables quick screening of a drug.

(2) Since collagen gel is a biologically derived gel, the characteristics are different on a lot basis. Further, since a difference in conditions such as a temperature also causes the gel characteristics to vary, variation between fabricated evaluation models increases.

On the other hand, since the evaluation model fabricated with the device 1 disclosed in the present specification uses a culture medium, variation between fabricated evaluation models can be reduced.

(3) In the case of Non-Patent Literature 2, the device 1 is entirely covered with collagen gel. Therefore, for example, in an attempt to determine an impact on a motor neuron when an electrical stimulation is given to a skeletal muscle tissue, it is difficult to give a selective electrical stimulation because of electrical leakage through the collagen gel.

On the other hand, in the evaluation model fabricated with the device 1 disclosed in the present specification, skeletal muscle tissues and motor neurons communicate with each other via only the first axon passage holes 451 (second axon passage holes 451'). Therefore, skeletal muscle tissues or motor neurons can be selectively electrically stimulated.

(4) In the case of Non-Patent Literature 2, since an axon extends in random directions in the collagen gel to reach a skeletal muscle tissue, it is not possible to adjust the axon directed to a skeletal muscle tissue.

On the other hand, the evaluation model fabricated with the device 1 disclosed in the present specification requires for an axon to pass through the first axon passage holes 451, and it is therefore possible to adjust the number or the interval of axons extending to the skeletal muscle tissue. Therefore, variation of fabricated evaluation models can be reduced.

When a fabricated evaluation model is used as an axonal degeneration neuropathy model, the device 1 including the third unit 4 having the first channel 42b and the second channel 42c is used to fabricate the evaluation model. Further, it is preferable to add steps of rupturing an axon between the second opening part 45a of the second channel 42c and the first opening part 45 of the first channel 42b and then reproducing an axon. Note that, when fabricating a model focusing in particular on the position at which an axon is ruptured and reproduced, the skeletal muscle tissue fabrication step (ST2) and the neuromuscular junction fabrication step (ST3) may be omitted. Further, when fabricating an axonal degeneration neuropathy model by using a motor neuron culturing device including the third unit 4 having the first channel 42b and the second channel 42c, it is preferable to add steps of rupturing an axon between the second opening part 45a of the second channel 42c and the first opening part 45 of the first channel 42b and then reproducing an axon after performing the motor neuron culture step (ST1).

[Embodiment of Screening Method]

Figure 11:
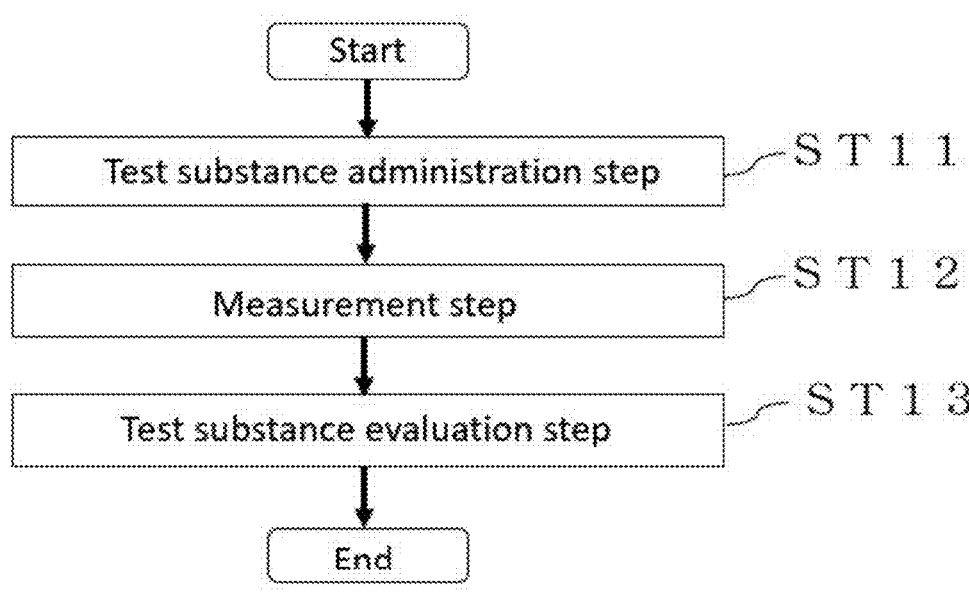
FIG. 11 is a flowchart of an embodiment of a screening method.

Next, an embodiment of a screening method will be described with reference to FIG. 11. The embodiment of the screening method is implemented by using the evaluation model fabricated by the fabrication method of the evaluation model described above. FIG. 11 is a flowchart of the embodiment of the screening method. The embodiment of the screening method includes a test substance administration step (ST11), an measurement step (ST12), and a test substance evaluation step (ST13).

In the test substance administration step (ST11), a test substance is administered to any one of a motor neuron, an axon extending from a cell body of the motor neuron, and a skeletal muscle tissue of a fabricated evaluation model. The test substance is not particularly limited as long as it is a substance known as pharmaceuticals such as a low molecular weight compound, a nucleic acid, an antibody, a protein, or the like. To stimulate a motor neuron to examine the impact on a skeletal muscle tissue by using the fabricated evaluation model, it is preferable to administer the test substance to the second culture tank. In the administration of a test substance, it is preferable to dissolve the test substance in the culture medium for the administration, if necessary. To stimulate an axon to examine the impact on a skeletal muscle tissue, it is preferable to administer a test substance to an axon. To administer a test substance to an axon, it is preferable to pour the test substance into the first channel 42b of the third unit 4 illustrated in the second embodiment. Alternatively, when the length of the axon is relatively long, the test substance may be administered to an axon near the first opening part 45 of the third unit 4 illustrated in the first embodiment. Alternatively, for example, a through hole penetrating to reach the axon channel 42 may be formed in the third base material 41 of the third unit 4 illustrated in FIG. 3B, and a test substance may be administered into the axon channel 42.

In the measurement step (ST12), the state of at least one of the motor neuron, the axon extending from a cell body of the motor neuron, and a skeletal muscle tissue that are resulted after the test substance is administered in the test substance administration step is measured. In the measurement step, the measurement method is not particularly limited as long as it can measure a change in the state of a motor neuron, an axon extending from a cell body of the motor neuron, and a skeletal muscle tissue before and after administration of a test substance. For example, to measure the state of the skeletal muscle tissue 10, it is preferable to measure the movement of the skeletal muscle tissue 10. The movement of the skeletal muscle tissue may be directly measured or may be indirectly measured. An example of a direct measurement method may be moving-image observation of the movement of the skeletal muscle tissue 10 using an image capture device. Further, since the skeletal muscle tissue 10 is formed between the pillars 23, contraction of the skeletal muscle tissue 10 causes a load on the pillars 23. Therefore, as an example of an indirect measurement method, a distortion sensor is arranged inside or on the surface of the pillar 23, and force applied to the distortion sensor is measured.

Measurement of the state of an axon may be, for example, measurement of an increase or decrease in the number, a change in the extension, the status of rupture and reproduction of an axon, or the like of axons due to an impact of a test substance. As a measurement method, measurement using an image capture device may be employed. Further, the measurement of the state of a motor neuron may be, for example, measurement of death or growth of a motor neuron due to the impact of a test substance, a change in the shape of a clump (spheroid) of motor neurons due to death or growth, or the like. As a measurement method, measurement using an image capture device may be employed.

In the test substance evaluation step (ST13), it is evaluated from the measurement result of the measurement step (ST12) whether or not the test substance works as a therapeutic agent against a neuromuscular disease. The evaluation may be such that a person evaluates the measurement result, or movement of a skeletal muscle tissue of a human body when a therapeutic agent is administered is stored in a storage unit in advance, and the test substance is evaluated to be therapeutically effective when movement similar to the case of administration of the therapeutic agent is measured. The neuromuscular disease is not particularly limited as long as it is a disease related to signaling between a motor neuron and a skeletal muscle tissue. For example, the neuromuscular disease may be a genetic disease caused by a gene variation, such as Amyotrophic Lateral Sclerosis (ALS) or Spinal and Bulbar Muscular Atrophy (SBMA). Further, the neuromuscular disease may be, for example, a disease other than genetic diseases, such as brachial plexus injury or facial nerve palsy, caused when an axon extending from a cell body of a motor neuron is mutated by a physical attack or a nerve toxic substance.

While Examples will be presented below to specifically describe the embodiments disclosed in the present application, these Examples are intended only for the purpose of illustration of the embodiments. These examples are not intended to limit or restrict the scope of the invention disclosed in the present application.

EXAMPLES

Example 1

[Fabrication of Device]

[1] Fabrication of Mold

First, a mole used for fabricating a device was fabricated in the following procedure.

(1) The mold photomask fabrication was performed by using laser lithography. Heidelberg DWL66FS (Heidelberg Instruments, Heidelberg, Germany) was used as the apparatus. CS HARDMASK BLANKS (CBL3006Cu-AZP, CLEAN SURFACE TECHNOLOGY, Kanagawa, Japan) was used as a photomask. This photomask has a chrome layer on a glass plate, and AZP1350 that is a photosensitive material is applied thereon. A pattern designed by laser was drawn on the photomask and developed by NMD3.

Figures 12A, 12B:
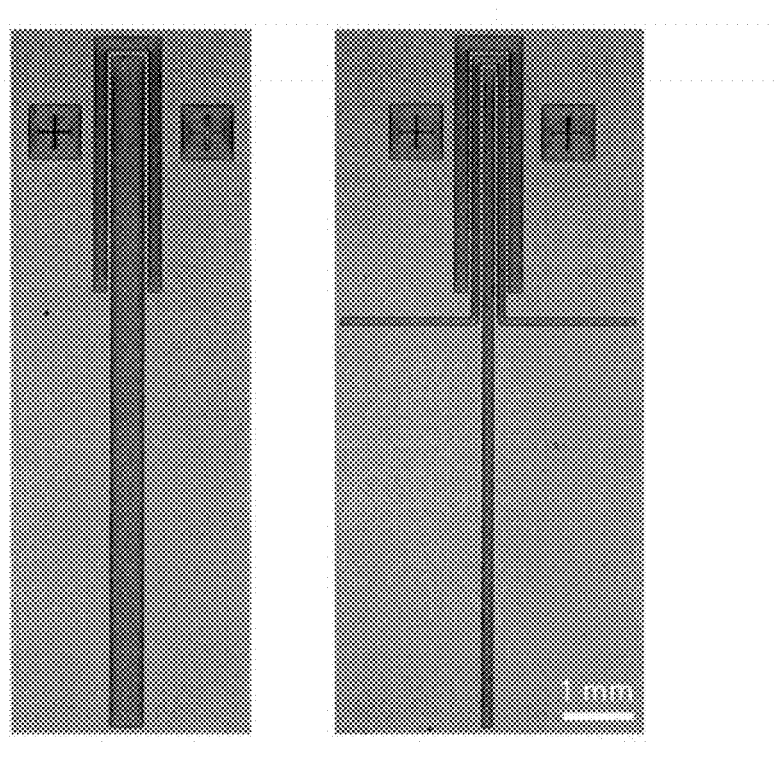
FIG. 12A and FIG. 12B are photograph substitutes for drawings, which represent photographs of a mold fabricated in Example 1.

(2) Next, the fabricated photomask was used to fabricate a mold. A mask aligner MA-6 (Suss Micro Tec AG) was used as an exposure apparatus. On a silicon wafer (Polishing Wafer (4PTP-1-100, GlobalWafers, Hsinchu, Taiwan)), SU-8 3005 (Nippon Kayaku Co., Ltd., Tokyo, Japan. Note that SU-8 3005 diluted two times with cyclopentanone (C0510, Tokyo Chemical Industry Co., Ltd., Tokyo, Japan) was used.) was placed up to the extent that 80 percent of the whole silicon wafer was hidden, spin coating was performed for 30 seconds after the rotation speed was increased up to 500 rpm at 100 rpm/sec, and subsequently, spin coating was performed for 30 seconds after the rotation speed was increased up to 3000 rpm at 300 rpm/sec. The silicon wafer was then heated (prebaked) at 95 degrees Celsius for 50 minutes, and a resulted silicon wafer and a photomask provided with a channel pattern were set in the MA-6 and exposed with ultraviolet ray for 40 seconds. The exposure causes SU-8 to solidify into the same shape as the pattern on the photomask. After the exposure, the silicon wafer was heated (postbaked) at 65 degrees Celsius for 50 seconds and 95 degrees Celsius for 20 seconds. From the above of the silicon wafer, SU-8 3050 (Nippon Kayaku Co., Ltd., Tokyo, Japan) was then placed up to the extent that 80 percent of the whole silicon wafer was hidden, and spin coating was performed for 30 seconds after the rotation speed was increased up to 2000 rpm at 100 rpm/sec. The silicon wafer was then heated at 95 degrees Celsius for 1 hour and was set in the MA-6 together with the photomask provided with a chamber pattern in turn, alignment to align the channel and the chamber was performed, and exposure was performed for 5 minutes. After the exposure, the silicon wafer was heated at 95 degrees Celsius for 8 minutes, immersed in SU-8 developer (Nippon Kayaku Co., Ltd., Tokyo, Japan) for about 40 minutes to remove excessive SU-8, and then immersed in isopropanol (166-04836, Wako, Tokyo, Japan). The fabricated molds are illustrated in FIG. 12A and FIG. 12B. FIG. 12A illustrates a mold corresponding to the axon channel of the first embodiment, and FIG. 12B illustrates a mold corresponding to an axon channel (the first channel plus the second channel) of the second embodiment. Hereafter, in the specification and the drawings, a device fabricated by using the mold illustrated in FIG. 12A may be referred to as "device a", and a device fabricated by using the mold illustrated in FIG. 12B may be referred to as "device b".

[2] Fabrication of Motor Neuron Culturing Device (3) First, PDMS mixed at a ratio of monomer:catalysis=10:1 (Dow Toray Co., Ltd., Sylgard 184) was placed on a mold, spin coating was performed at 300 rpm for 30 seconds, and PDMS was heated at 70 degrees Celsius for 1 hour and was solidified.

(4) PDMS(i) solidified by (3) described above was removed from the mold, and thereby the third unit in which one face of the axon channel 42 and the first opening part 45 (second opening part 45a) was opened was fabricated. Next, PDMS(ii) in which the second culture tank 32 was formed and a PDMS thin film(iii) used for bottom fabrication were prepared. PDMS(i) was attached to the PDMS thin film(iii) used for bottom fabrication with the opened surface of PDMS(i) facing down. Further, PDMS(ii) in which the second culture tank 32 was formed was attached to the upper surface of PDMS(i). Note that, before attachment of PDMS of (i) to (iii), the surfaces to be attached were plasmaprocessed to enable the PDMS to be adhered to each other. PLASMA CLEANER (PDC-32G, HARRICK PLASMA, New York, USA) was used for the plasma process.

Figure 13:
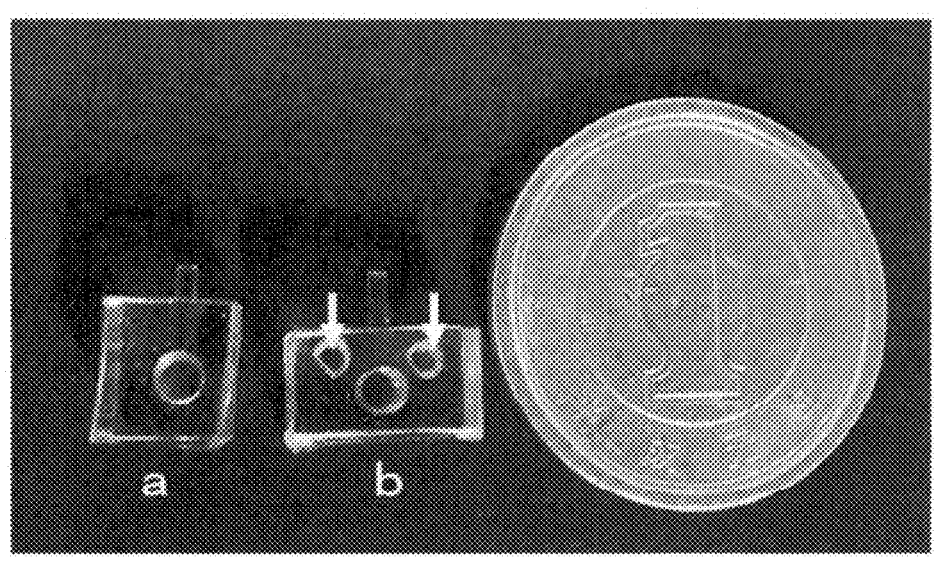
FIG. 13 is a photograph substitute for a drawing, which is a photograph of a motor neuron culturing device fabricated in Example 1.

(5) Protrusions or the like of the PDMS attached in (4) described above were cut off by a knife to fabricate a device. FIG. 13 is a photograph of the fabricated motor neuron culturing devices a and b. Note that the arrow portions of the motor neuron culturing device b represent a test substance supply hole and a test substance collection hole that are formed in the second base material 31 and communicate with the first channel 42*b*.

Figure 14:
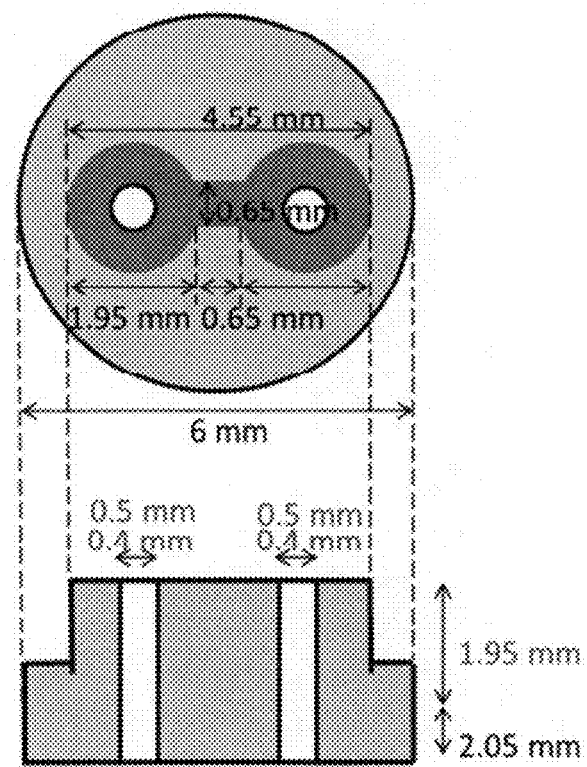
FIG. 14 is a mold drawing used for fabricating a first unit of Example 1.

[3] Fabrication of First Unit (6) The first unit 2 was fabricated by using a mold fabricated by Teflon (see FIG. 14) to pour and heat PDMS at 70 degrees Celsius for 1 hour to solidify the PDMS. After removal from the mold, a disc fabricated with thin film PDMS was placed on the pillar of the first unit. PDMS of 0.2 g was placed on a Teflon sheet, and the thin film disc was spin-coated for 30 seconds after the rotation speed was increased to 1000 rpm in 30 seconds. The disc was then heated at 70 degrees Celsius for 1 hour to solidify the PDMS. Furthermore, PDMS of 0.2 g was placed, and spin coating was performed for 30 seconds after the rotation speed was increased to 2000 rpm in 30 seconds. A circle with a diameter of 1.5 mm was cut out from the PDMS thin film by using biopsy (8-5845-02, kai industries, Japan), attached to the upper part of the pillar of the first unit, and heated at 70 degrees Celsius for 1 hour, and thereby the thin film disc was fixed to the tip of the pillar.

[4] Fabrication of Device

The motor neuron culturing device fabricated in [2] described above and the first unit 2 fabricated in [3] described above were joined and heated with PDMS being thinly applied and thereby solidified. FIG. 15 represents photographs of the fabricated devices a and b. FIG. 15A is a photograph of the fabricated devices a and b taken from above, and FIG. 15B is a photograph of the fabricated devices a and b taken from diagonally above.

Example 2

[Fabrication of Evaluation Model]

An evaluation model was fabricated by materials and methods illustrated below.

(1) Culture of iPS Cells (1-1) Culture of Undifferentiated iPS Cells

First, a culture method of human iPS cells (201B7) will be illustrated. Stemfit (registered trademark) (AK02N, Ajinomoto, Tokyo, Japan) was used as a culture medium for cell growth. Culture was performed in a cell culture T25 flask (430639, CORNING, New York City, USA) within a $CO_2$ incubator under 5% $CO_2$ and 95% air at 37 degrees Celsius. Laminin coating was performed on the used flask. The laminin coating was performed by a scheme to add 3 ml of PBS, add 25 µl of iMatrix-511 (381-07363, Wako, Tokyo, Japan) thereto, and incubate the mixture in a $CO_2$ incubator for 1 hour or longer. With respect to a passage operation, 2.5 ml of AK02N with iMatrix solution being contained was added and settled after coating was performed, then the solution was removed, and 5 ml of AK02N was added. Then, 5 µl of ROCK inhibitor Y-27632 (08945-71, Nacalai Tesque Co., Ltd., Kyoto, Japan) was added, and the mixture was incubated in a $CO_2$ incubator until immediately before seeding. The culture medium of cells in a subconfluent state was removed, and after the cells were washed once with PBS, 1 ml of a trypsin solution in which TrypLE (registered trademark) Select CTS (registered trademark) (A12859-01, Life Technologies, California, USA) and UltraPure (registered trademark) 0.5M EDTA pH 8.0 (15575-038, Life Technologies, California, USA) were mixed at 1:1 was added, and the solution was incubated in a $CO_2$ incubator for 4 minutes. The trypsin solution was removed, the cells were washed once with PBS, 2.5 ml of AK02N was then added, and cells were collected by a cell scraper (99002, TPP, Switzerland). After the collected cells were suspended 10 times by using a 1-ml pipetman, the number of cells was calculated by TC20 (registered trademark) full automatic cell counter (California, USA). The cells were then seeded in a T25 flask so as to have 32500 cells, and the cells were incubated in a $CO_2$ incubator. To remove Y-27632, the culture medium was replaced after 24 hours from the seeding. Subsequently, the culture medium was replaced every 48 hours, and when the cells became close to a confluence state, the culture medium was replaced every 24 hours.

(1-2) Differentiation Induction of iPS Cells to Motor Neurons

Undifferentiated iPS cells were suspended in 10 ml of Stemfit and cultured in a 5% $CO_2$ incubator at 37 degrees Celsius for 1 to 2 days until spheroids were made in 60 mm dish. After the spheroids were formed, cells were precipitated by natural precipitation, and supernatant of a culture medium was removed, the cells were then suspended in an EB culture medium and cultured in a 100-mm dish. Table 1 illustrates the final concentration of respective culture medium additives in a differentiation culture medium from the start of differentiation induction (DAY 0) to the end of differentiation induction (DAY 14) of a nerve. Further, FIG. 16 illustrates the overview of differentiation induction. Note that FIG. 16 is quoted from "Shimojo et al., Mol Brain. 2015 Dec. 1; 8(1): 79". Replacement of the differentiation culture medium was performed in accordance with the schedule indicated in FIG. 16, and the stated culture medium additives were added to a culture medium in which 5% KSR (Knockout Serum Replacement, 10828028, Sigma-Aldrich, Missouri, USA) was mixed to DMEM/F-12 and cultured, respectively.

TABLE 1

| Day | TGF-βR inhibitor: SB431542 | GSK3β inhibitor: CHIR99021 | BMP inhibitor: LDN-193189 | Retinoic acid | Purmorphamine |
|---|---|---|---|---|---|
| 1 | 3 µM | 3 µM | 300 µM | | |
| 2 | 3 µM | 3 µM | 300 µM | 1 µM | |
| 4 | | | | 1 µM | 1 µM |
| 7 | | | | 1 µM | 1 µM |
| 10 | | | | 1 µM | 1 µM |

SB431542 (13031, Funakoshi, Japan)
CHIR99021 (13122 Funakoshi, Japan)
LDN-193189 (LDN-002, Funakoshi, Japan)
Ratinoic acid (186-01114, Wako, Tokyo, Japan)
Purmorphamine (540220, Calbiochem, USA)

(2) Passage Culture of Skeletal Muscle Cells

A human skeletal muscle Hu5KD3 (transferred from National Center for Geriatrics and Gerontology) was used for skeletal muscle cells, and culture was performed in the following procedure. In the culture of these cells, collagen coating on the bottom was performed. Collagen (Cellmatrix typeI-C: Nitta Gelatin Corporation, Osaka, Kyoto, Japan) was dissolved in 0.02 N acetic acid to fabricate a collagen solution with a concentration of 50 µg/ml. This solution was put in and allowed to stand still at normal temperature for 1 hour with the bottom being filled with the collagen solution. DMEM (20% Fetal Bovine Serum, 2 mM L-glutamine (073-05391, Wako, Tokyo, Japan), 0.5% penicillin/strepto- mycin, 2% Ultroser G serum substitute (15950-017, Pall, New York City, USA)) was used for the growth culture medium.

(3) Co-Culture of Motor Neurons and Three-Dimensional Skeletal Muscle Tissues Using a Device.

Co-culture was performed in the following procedure by using the device fabricated in Example 1. FIG. 17 is a diagram illustrating a co-culture procedure. Note that, for convenience in experiments for culture medium replacement or the like, the device fabricated in Example 1 was fixed to the bottom of the well of the 12-well plate. After the device and the well were fixed, UV sterilization was performed for 1 hour. Then, a plasma process (11 W, 30 seconds) was performed, and Matrigel coating was performed. Matrigel (354234, CORNING, New York City, USA) was diluted 30 times in serum-free DMEM/F-12 (Dulbecco's Modified Eagle Medium: Nutrient Mixture F-12) (042-30555, Wako, Tokyo, Japan), and the diluted solution was put in the device. The device was allowed to stand still at normal temperature for 3 hours with the whole bottom of the device being filled with the Matrigel solution. At this time, the device was allowed to stand still while being degassed so that the Matrigel solution spread to the whole channel. The whole Matrigel solution was then aspirated and removed by an aspirator. Due to this process, since proteins contained in the Matrigel are adsorbed to the second culture tank 32 and the axon channel 42, this facilitates motor neurons to adsorb to the second culture tank 32 and axons to adsorb to the axon channel 42.

After the end of the Matrigel coating, several motor neurons induced from human iPS cells were seeded in the second culture tank of the device in a spheroid state. A motor nerve culture medium (MN culture medium) in which culture medium additives indicated below were added to KBM Neural Stem Cell Kit (Ser. No. 16/050,100, Kohjin bio, Saitama, Japan) was used for culture of motor nerves after seeding. The culture medium additives are 2% B-27 (17504-044, Thermofisher, Massachusetts, USA) and 1% non-essential amino acids; NEAA (Ser. No. 11/140,050, Life technologies, California, USA), 1 µM cAMP (D-0260, Sigma-Aldrich, Missouri, USA) and 10 ng/ml brain derived neurotrophic factor; BDNF (248-BD-025, R&D, Minneapo- lis, USA) and 10 ng Glial cell-derived neurotrophic factor; GDNF (212-GD-050, R&D, Minneapolis, USA) and 10 ng/ml Insulin-like growth factors-1; and IGF-1 (291-G1- 050, R&D, Minneapolis, USA), 50 nM RA, 500 nM Pur- morphamine, and 200 ng/ml Ascorbic Acid (012-04802, Wako, Tokyo, Japan). At this time, an MN culture medium containing no cell was added to the first culture tank.

On the second day from the motor neuron seeding, human skeletal muscle cell Hu5KD3 was seeded in the first culture tank. Specifically, cells that had been cultured in a T-75 flask were collected in the same manner as the passage operation, the number of cells was measured, and the cells were seeded in the first culture tank so as to have $2\times10^6$ cells/ml in a solution containing fibrinogen (F8630, Sigma-Aldrich, Mis- souri, USA), Matrigel, Thrombin from bovine plasma (Thrombin: T4648, Sigma-Aldrich, Missouri, USA), and 2×DMEM. Table 2 illustrates the final solution composition. An MN culture medium of 3 ml was put in so as to fill the whole well including the device, and tissues were formed, grown, and differentiated. To prevent breakdown of muscle tissues, 6-Amino caproic Acid (A2504, Sigma-Aldrich, Mis- souri, USA) (6AA) was added to have 2.0 mg/ml. A three- dimensional skeletal muscle tissue formed on the seventh day from the motor neuron seeding and the other end part 44 of the third unit 4 were joined by Matrigel so that the skeletal muscle tissue and the other end part 44 were not displaced due to an impact or the like. Note that the joining of Matrigel is an auxiliary procedure and may be omitted. The culture medium was replaced by half the amount every two days. The evaluation model was fabricated with the above proce- dure.

TABLE 2

| Coil suspension | 48% |
|---|---|
| Fibrinogen | 20% |
| 2 × DMEM | 20% |
| Matrigel | 10% |
| Thrombin (2%) | 2% |

FIG. 18A is an enlarged photograph of a view around the first opening part of the third unit of the evaluation model fabricated by using the device a. Further, FIG. 18B is an enlarged photograph of a view around the first opening part of the third unit of the evaluation model fabricated by using the device b. In the evaluation models fabricated by using the device a and the device b, it was confirmed that an axon extended in the axon channel and the axon passed through the first axon passage hole (second axon passage hole).

[Staining of Neuromuscular Junction]

In the evaluation model fabricated by co-culturing motor neurons and skeletal muscle cells, it was confirmed by fluorescent staining of myotube cells whether or not a neuromuscular junction was formed. First, a solution in which the culture medium used in the culture of skeletal muscle cells and 4% PFA/PBS (161-20141, WAKO, Tokyo, Japan) were mixed half and half was put in a well and allowed to stand still at normal temperature for 5 minutes. Then, the solution was removed, 4% PFA/PB was put in the well and allowed to stand still at normal temperature for 15 minutes for solidification. The 4% PFA/PB was removed, and PBS was put in and allowed to stand still at normal temperature for 10 minutes, which was repeated three times for washing. Then, the PBS was removed, 0.3% TritonX- 100 (T8787-250 ml, Sigma Aldrich, Missouri, USA)/PBS was put therein, and the mixture was passed through a membrane at normal temperature for 5 minutes. Also in this process, washing was performed with PBS three times, the primary antibody/a basic liquid was put therein and allowed to stand still for 1 hour for blocking. For the composition of the basic solution, 10% Goat serum (S-1000, Vector Labo- ratories, California, USA)+0.01% TritonX-100/PBS was used. After blocking, the basic liquid mixed with the primary antibody to have a concentration of 2 µg/ml was put therein and reacted at 4 degrees Celsius overnight. The primary antibody used for immunostaining of myotube cells was TUJ1 (845501, Biolegend, USA). The solution was removed on the next day, washing was performed with PBS three times, and the basic liquid mixed with the secondary anti- body to have a concentration of 4 µg/ml was put therein and reacted for 1 hour. The used secondary antibody was CF543 (registered trademark) Goat anti-rabbit IgG(H+L), Highly Vross-adsorbed, 2 mg/ml (20300, BIOTIUM, California, USA). For staining of acetylcholine receptors, Fluoredcein- alpha-bungarotoxin (PK-CA707-00011, PromoKine, Heidelberg, Germany) obtained by putting a fluorescent pigment on α-bungarotoxin that is antagonist was added to have the final concentration of 4 μg/ml. Washing was performed with PBS three times, and observation was performed with a confocal microscope.

Figure 19:
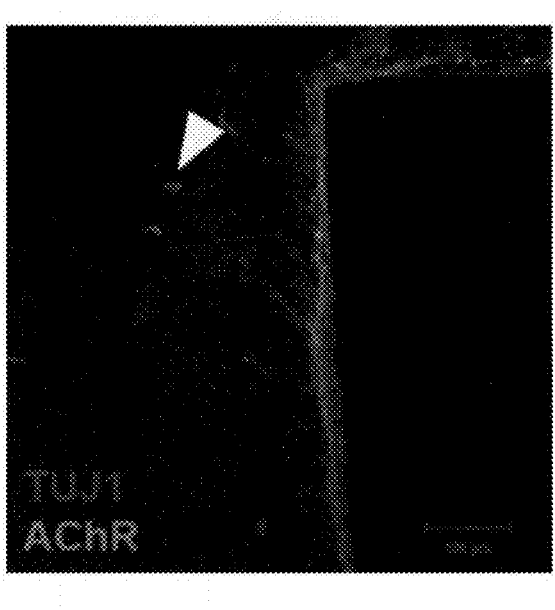
FIG. 19 is a photograph substitute for a drawing, which is a photograph obtained by staining a neuromuscular junction of the evaluation model fabricated in Example 2 and capturing an image by using a confocal microscope.

FIG. 19 is a photograph captured by a confocal microscope in which the staining portion at the tip of the triangle in FIG. 19 indicates that an aggregation of acetylcholine receptors was stained. Aggregated acetylcholine receptors are present in a neuromuscular junction. Because staining of an aggregation of acetylcholine receptors was confirmed in the fabricated evaluation model, it was confirmed that a neuromuscular junction was formed in the fabricated evaluation model.

[Confirmation of Phenotype of Neuromuscular Junction]

Next, to confirm formation of a neuromuscular junction in a functional manner, confirmation of contraction of a skeletal muscle tissue caused by a single stimulation to a motor neuron was performed with the evaluation model fabricated using the device a. Glutamic acid (070-00502, Wako, Tokyo, Japan) was used to stimulate a motor neuron. It is known that glutamic acid is a neurotransmitter that can work on a lower motor nerve and thereby facilitate nerve firing. First, an MN culture medium in which glutamic acid was dissolved to have the final concentration of 400 μM was added to the second culture tank. To confirm that a stimulation from a motor nerve has been transmitted to a skeletal muscle tissue and is triggering contraction, tetrodotoxin (TTX, 206-11071, Wako, Tokyo, Japan) was added to the second culture tank to have the final concentration of 2 μM after about 20 seconds. Tetrodotoxin selectively inhibits the Na channel of an excitable membrane of a motor nerve. Contraction of a skeletal muscle tissue, which was observed before and after addition of a drug, was captured as a moving image by using BZ-X710, and the view of contraction was graphed by using moving-image analysis software PV Studio 2D (OA Science, Miyazaki, Japan).

Figure 20:
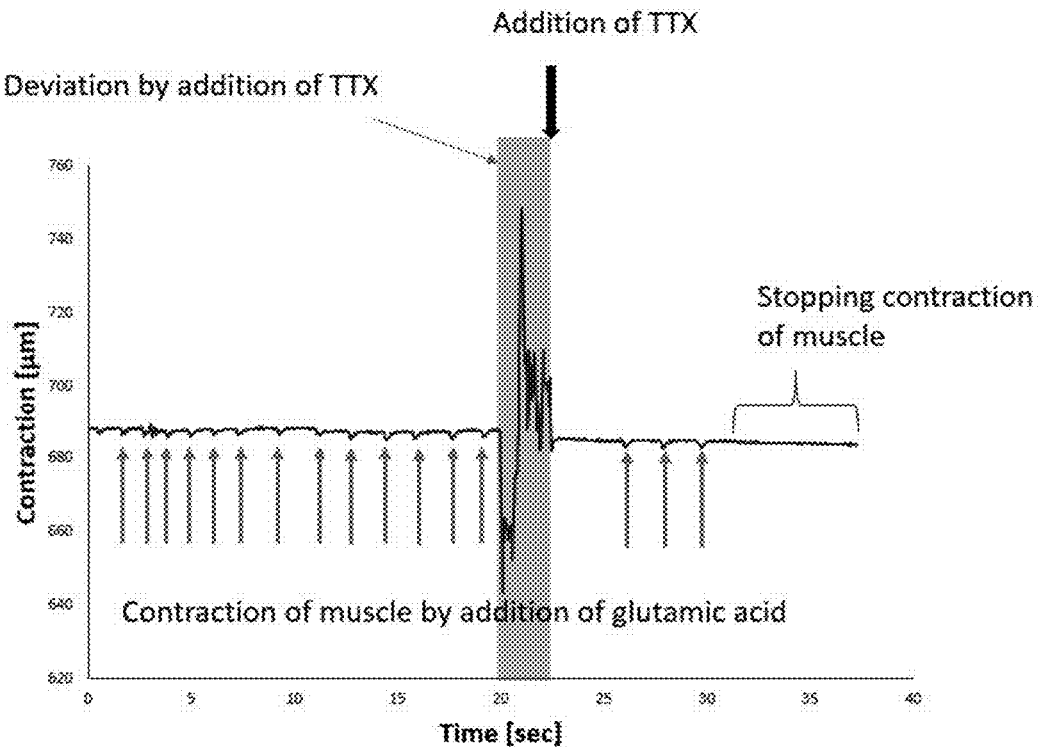
FIG. 20 is a graph illustrating a contraction of a skeletal muscle tissue before and after a drug is added to the evaluation model fabricated in Example 2.

FIG. 20 is a graph illustrating contraction of a skeletal muscle tissue observed before and after addition of a drug. As is clear from FIG. 20, it was confirmed that administration of glutamic acid to the second culture tank, that is, to motor neurons causes contraction of a skeletal muscle tissue. Further, it was confirmed that administration of tetrodotoxin stops contraction of a skeletal muscle tissue. From the above results, it was confirmed that, in the evaluation model fabricated by using the device disclosed in the present specification, an axon extending from a cell body of a motor neuron joins to a skeletal muscle tissue and forms a neuromuscular junction. Further, because the degree of contraction of a skeletal muscle tissue varied in accordance with addition of drugs, it was confirmed that a therapeutic agent against a neuromuscular disease can be screened by using the evaluation model disclosed in the present specification.

[Staining of Axon]

An axon was stained with the following procedure by using the evaluation model fabricated by using the device b. For a staining reagent, Cell Brite (registered trademark) Cytoplasmic Membrane Dyes (30021, BIOTIUM, California, USA) was used. A solution in which a reagent and a culture medium were mixed at a ratio of reagent:culture medium=5 μl:1 ml was supplied from the test substance supply hole, and the staining reagent was poured in the first channel to react for 30 minutes or longer. The first channel was then washed with the using culture medium and observed by using a microscope.

Figure 1:
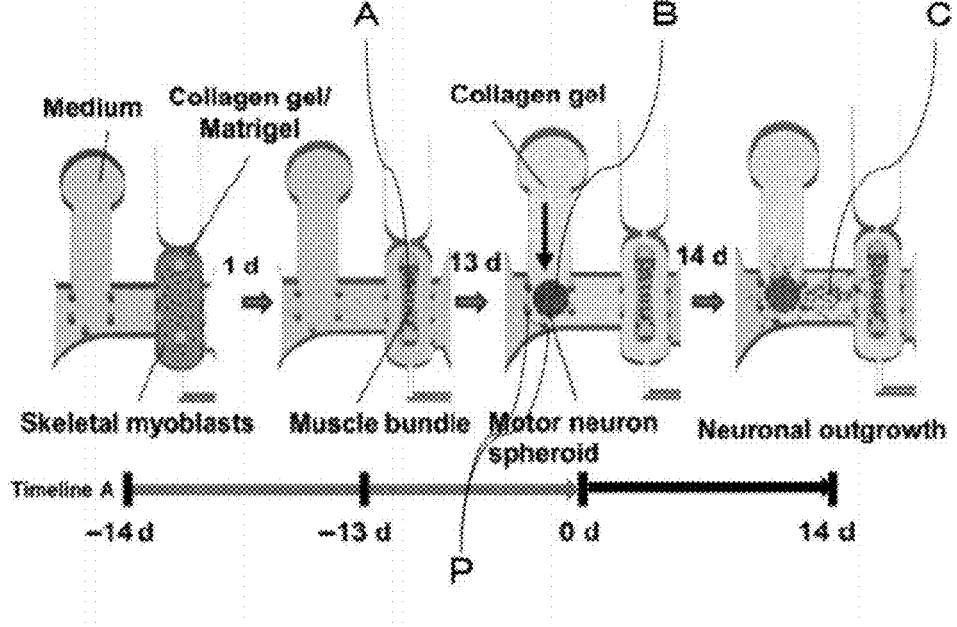
FIG. 1 is a diagram illustrating an example of a conventional art for a device (evaluation model).
Figure 2:
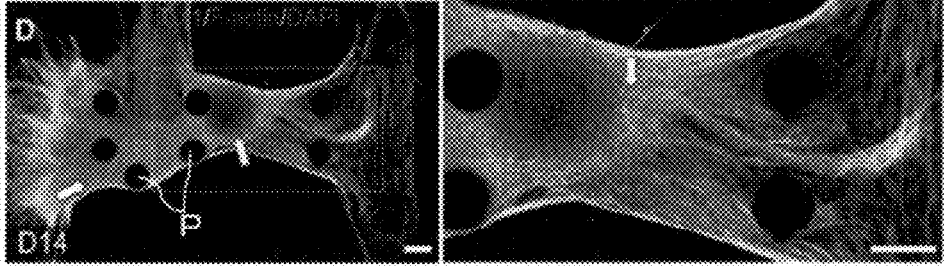
FIG. 2 is a photograph substitute for a drawing and illustrates that, in an evaluation model fabricated by using a conventional art device, motor neurons and a skeletal muscle tissue are fused as time elapses.

FIG. 21A and FIG. 21B are photographs when observed by using a microscope, which are photographs with different brightness at the same place. The bright portion at the arrow point in each photograph is the stained axon. It was confirmed that it is possible to selectively stain only the axon in the first channel by supplying a staining reagent into the first channel. Therefore, it was confirmed that, instead of a staining reagent, a test substance of a therapeutic agent against a neuromuscular disease can be used for screening a therapeutic agent that specifically affects an axon. Further, in the evaluation model fabricated by co-culturing motor neurons and skeletal muscle cells by using the device fabricated in Example 1, no fusion of a motor neuron and a skeletal muscle cell was found before the evaluation model was used for another experiment on the 27th day. As illustrated in FIG. 2, it is indicated that, in the evaluation model fabricated by using the device disclosed in Non-Patent Literature 2, a motor neuron climbed over the pillar on the 14th day after the start of co-culture. Therefore, with fabrication of the evaluation model by using the device disclosed in the present specification, evaluation can be performed in a state where a motor neuron, an axon extending from a cell body of the motor neuron, and a skeletal muscle tissue are separated from each other for longer time than the evaluation model fabricated by using the conventional device.

Example 3

[Confirmation of Rupture and Reproduction of Axon]

Motor neurons were cultured by using the device 1*b* fabricated in Example 1 with the same procedure as (1) described above of Example 2. After the end of the culture, a culture medium was poured from the one end 42*b*1 of the first channel 42*b* into the first channel 42*b* with a shear stress of about 60 Pa by using a syringe pump. FIG. 22A to FIG. 22C are enlarged photographs of a view around the second opening part 45*a* of the third unit 4 after the end of the culture. FIG. 22A is a photograph at the end of culture of motor neurons, and axons (the arrows in FIG. 22A) passing through the first channel 42*b* from the second opening part 45*a* and extending to the first opening part 45 were confirmed. FIG. 22B is a photograph after about 30 seconds elapsed after the culture medium was poured with a shear stress of about 60 Pa, and it was confirmed that the axons were ruptured. FIG. 22C is a photograph after about 24 hours elapsed after the axons were ruptured, and it was confirmed that the axons were reproduced (the arrows in FIG. 22C). From the above results, it was confirmed that the use of the device disclosed in the present application enables rupture and reproduction of an axon.

INDUSTRIAL APPLICABILITY

The use of the device, the evaluation model fabricated by using the device, and the screening method using the evaluation model disclosed in the present application enables screening of therapeutic agents against neuromuscular diseases. Therefore, the device, the evaluation model fabricated by using the device, and the screening method using the evaluation model disclosed in the present application are useful for drug discovery at medical institutions, universities, companies, research institutes, or the like.

LIST OF REFERENCE SYMBOLS

1, 1*a* to 1*d* co-culturing device
2 first unit
3 second unit
4 third unit
5 motor neuron culturing device
5*a* motor neuron culturing device 6 cover
10 skeletal muscle tissue
11 axon
21 first base material
22 first culture tank
23 pillar
24 cut-off
31 second base material
32 second culture tank
33 third unit insertion part
41 third base material
42 axon channel
42a virtual axon channel
42b first channel
42b1 one end of first channel
42b2 the other end of first channel
42c second channel
42c1 one end of second channel
42c2 the other end of second channel
42c3 second channel wall surface
43 one end part of third unit
44 the other end part of third unit
45 first opening part
45a second opening part
211 bottom of first base material
212 side wall surface of first base material
221 first culture medium supply hole
231 one end of pillar
232 the other end of pillar
321 second culture medium supply hole
411 third base material opening part
421 axon channel opening
422 the other end of axon channel
423 slit
431 side surface of one end part
451 first axon passage hole
451' second axon passage hole
451a, 451a' first opening face
451b, 451b' second opening face
500 multi-well plate
501 base material
502 well
503 pair of electrodes
504 circuit

The invention claimed is:

1. A co-culturing device for a motor neuron and a skeletal muscle cell, the device comprising:
a first unit for skeletal muscle tissue formation;
a second unit for motor neuron culture;
at least one third unit for causing the first unit and the second unit to communicate with each other; and
at least one pillar serving as a scaffold for the skeletal muscle tissue formation,
wherein the first unit includes
a first base material, and
a first culture tank formed in the first base material,
wherein the second unit includes
a second base material, and
a second culture tank formed in the second base material,
wherein the third unit includes
a third base material, and
an axon channel which is formed in the third base material and includes an inlet opening and an outlet opening, and through which a bundle of axons passes, wherein the inlet opening of the third unit is configured to be connected to the second unit and configured to cause the axon channel and the second culture tank to communicate with each other when the third unit is connected to the second unit,
wherein a first opening member is attached to a periphery of the outlet opening to close the outlet opening of the third unit, and includes one or more first axon passage holes that pass through the first opening member from a first surface of the first opening member facing the axon channel to a second surface of the first opening member opposite to the first surface,
wherein the outlet opening of the third unit faces the first unit,
wherein the first axon passage hole has a size through which an axon passes while neither a motor neuron nor a skeletal muscle cell passes, and
wherein at least a part of the pillar is arranged in the first culture tank.

2. The device according to claim 1,
wherein a height of the axon channel is 30 μm to 100 μm.

3. The device according to claim 1,
wherein a height of the third unit is lower than a height of the first unit and/or second unit.

4. A co-culturing device for a motor neuron and a skeletal muscle cell, the device comprising:
a first unit for skeletal muscle tissue formation;
a second unit for motor neuron culture;
at least one third unit for causing the first unit and the second unit to communicate with each other; and
at least one pillar serving as a scaffold for the skeletal muscle tissue formation,
wherein the first unit includes
a first base material, and
a first culture tank formed in the first base material,
wherein the second unit includes
a second base material, and
a second culture tank formed in the second base material,
wherein the third unit includes
a third base material, and
an axon channel which is formed in the third base material and includes an inlet opening and an outlet opening, and through which a bundle of axons passes,
wherein the inlet opening of the third unit is configured to be connected to the second unit and configured to cause the axon channel and the second culture tank to communicate with each other when the third unit is connected to the second unit,
wherein a first opening member is attached to a periphery of the outlet opening to close the outlet opening of the third unit, and includes one or more first axon passage holes that pass through the first opening member from a first surface of the first opening member facing the axon channel to a second surface of the first opening member opposite to the first surface,
wherein the outlet opening of the third unit faces the first unit,
wherein the first axon passage hole has a size through which an axon passes while neither a motor neuron nor a skeletal muscle cell passes,
wherein at least a part of the pillar is arranged in the first culture tank, wherein the axon channel includes
    a first channel, and
    a second channel having an inlet opening and an outlet opening and disposed inside the first channel,
wherein the first opening member is formed so as to be in contact with the first channel,
wherein the inlet opening of the second channel is configured to communicate with the second culture tank, and a second opening member is attached to a periphery of the outlet opening of the second channel to close the outlet opening of the second channel,
wherein one or more second axon passage holes are formed in the second opening member, which pass through the second opening member from a first surface of the second opening member facing the second channel to a second surface of the second opening member opposite to the first surface of the second opening member, and each of the second axon passage holes has a size through which an axon passes while neither a motor neuron nor a skeletal muscle cell passes,
wherein in a cross section cutting the first channel and the second channel, the first channel and the second channel are separated from each other by walls, and
wherein a part of the first channel exists between the first surface of the first opening member and the second surface of the second opening member.

5. The device according to claim 1, wherein two or more third units are stacked.

6. The device according to claim 1,
wherein a positional relationship of the first unit, the second unit, the one or more third units, and the pillar is arranged such that
when two or more pillars are included, any of virtual planes connecting the two or more pillars intersects a virtual axon channel of the axon channel virtually extending to the first culture tank, or
when only one pillar is provided, a virtual plane formed by the one pillar or a virtual plane formed by the pillar and the outlet opening of the third unit intersects a virtual axon channel of the axon channel virtually extending to the first culture tank.

7. The device according to claim 6, wherein two pillars are included, one end of each of the pillars is connected to the first base material, and the other end is arranged in the first culture tank in a cantilevered manner.

8. The device according to claim 1,
wherein the size of the first axon passage hole is formed such that
the minimum distance is greater than or equal to 0.5 μm and less than or equal to 2.5 μm, or
the minimum distance is greater than or equal to 0.5 μm, and the sectional area is less than or equal to 60 μm².

9. The device according to claim 1,
wherein motor neuron culturing devices are each fabricated by the second unit and the third unit being connected to each other, and
wherein two or more of the motor neuron culturing devices are arranged to the first unit.

10. The device according to claim 1,
wherein a motor neuron culturing device is fabricated by connecting two or more third units to the second unit, and wherein the first unit is arranged to the outlet opening of any of the third units.

11. The device according to claim 1,
wherein a height of the axon channel is lower than a height of the first culture tank and/or the second culture tank.

12. The device according to claim 2,
wherein a height of the axon channel is lower than a height of the first culture tank and/or the second culture tank.

13. The device according to claim 2,
wherein a height of the third unit is lower than a height of the first unit and/or second unit.

14. The device according to claim 11,
wherein a height of the third unit is lower than a height of the first unit and/or second unit.

15. A co-culturing device for a motor neuron and a skeletal muscle cell, the device comprising:
a first unit for skeletal muscle tissue formation;
a second unit for motor neuron culture;
at least one third unit for causing the first unit and the second unit to communicate with each other; and
at least one pillar serving as a scaffold for the skeletal muscle tissue formation,
wherein the first unit includes
    a first base material, and
    a first culture tank formed in the first base material,
wherein the second unit includes
    a second base material, and
    a second culture tank formed in the second base material,
wherein the third unit includes
    a third base material, and
    an axon channel which is formed in the third base material and includes an inlet opening and an outlet opening, and through which a bundle of axons passes,
wherein the inlet opening of the third unit is configured to be connected to the second unit and configured to cause the axon channel and the second culture tank to communicate with each other when the third unit is connected to the second unit,
wherein a first opening member is attached to a periphery of the outlet opening to close the outlet opening of the third unit, and includes one or more first axon passage holes that pass through the first opening member from a first surface of the first opening member facing the axon channel to a second surface of the first opening member opposite to the first surface,
wherein the outlet opening of the third unit faces the first unit,
wherein the first axon passage hole has a size through which an axon passes while neither a motor neuron nor a skeletal muscle cell passes,
wherein at least a part of the pillar is arranged in the first culture tank, and
wherein when the third unit is connected to the second unit and the second unit is connected to the first unit, the third unit is not in direct contact with the first unit.

* * * * *